(12) United States Patent
Trzaska et al.

(10) Patent No.: US 10,017,505 B2
(45) Date of Patent: Jul. 10, 2018

(54) CRYSTALLINE FORMS OF A BACE INHIBITOR, COMPOSITIONS, AND THEIR USE

(71) Applicant: Merck Sharp & Dohme Corp., Rahway, NJ (US)

(72) Inventors: Scott Trzaska, Raritan, NJ (US); Zachary E. Dance, Robbinsville, NJ (US); Yong Liu, Princeton, NJ (US); Richard John Varsolona, Scotch Plains, NJ (US); Gregory York, Lebanon, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/514,584

(22) PCT Filed: Sep. 25, 2015

(86) PCT No.: PCT/US2015/052096
§ 371 (c)(1),
(2) Date: Mar. 27, 2017

(87) PCT Pub. No.: WO2016/053767
PCT Pub. Date: Apr. 7, 2016

(65) Prior Publication Data
US 2017/0233383 A1     Aug. 17, 2017

Related U.S. Application Data

(60) Provisional application No. 62/057,675, filed on Sep. 30, 2014.

(51) Int. Cl.
*C07D 417/12* (2006.01)
*C07C 309/30* (2006.01)

(52) U.S. Cl.
CPC .......... *C07D 417/12* (2013.01); *C07C 309/30* (2013.01); *C07B 2200/13* (2013.01)

(58) Field of Classification Search
CPC .................................................. C07D 417/12
USPC ........................................................... 544/80
See application file for complete search history.

(56) References Cited

U.S. PATENT DOCUMENTS

2012/0183563 A1     7/2012  Scott et al.

FOREIGN PATENT DOCUMENTS

| WO | 2016025359 A1 | 2/2016 |
| WO | 2016025364 A1 | 2/2016 |

OTHER PUBLICATIONS

International Search Report of PCT/US2015/052096 dated Dec. 22, 2015, 11 pages.
Pubchem, SID 121271204, May 16, 2011, pp. 1-5 ,URL: http://pubchem.ncbi.nih.gov/substance/121271204, p. 3, formula.
Pubchem, SID 198434380, Aug. 23, 2014, pp. 1-7, URL: http://pubchem.ncbi.nih.gov/substance/198434380, p. 3, formula.

*Primary Examiner* — Kahsay Habte
(74) *Attorney, Agent, or Firm* — Keith D. MacMillan; Catherine D. Fitch

(57) ABSTRACT

The present invention provides four crystalline forms of verubecestat, as well as pharmaceutically acceptable compositions thereof, each of which may be useful in treating, preventing, ameliorating, and/or delaying the onset of an Aβ pathology and/or a symptom or symptoms thereof. Non-limiting examples of such Aβ pathologies, including Alzheimer's disease, are disclosed herein.

19 Claims, 12 Drawing Sheets

CRYSTALLINE FORMS OF A BACE INHIBITOR, COMPOSITIONS, AND THEIR USE

FIELD OF THE INVENTION

This invention provides two novel crystalline forms of verubecestat (described below), a potent inhibitor of BACE-1 and BACE-2, pharmaceutically acceptable compositions thereof, and methods for their preparation and use in treating, preventing, ameliorating, and/or delaying the onset of an Aβ pathology and/or a symptom or symptoms thereof, such as Alzheimer's disease. The present invention also provides a novel synthesis of verubecestat.

BACKGROUND

Amyloid beta peptide ("Aβ") is a primary component of β amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis (β2 microglobulins and complications arising therefrom), neurodegenerative diseases such as scrapie, bovine spongiform encephalitis, Creutzfeld-Jakob disease, traumatic brain injury and the like.

Aβ peptides are short peptides which are made from the proteolytic break-down of the transmembrane protein called amyloid precursor protein ("APP"). Aβ peptides are made from the cleavage of APP by β-secretase activity at a position near the N-terminus of Aβ, and by gamma-secretase activity at a position near the C-terminus of Aβ. (APP is also cleaved by α-secretase activity, resulting in the secreted, non-amyloidogenic fragment known as soluble APPα.) Beta site APP Cleaving Enzyme-1 ("BACE-1") is regarded as the primary aspartyl protease responsible for the production of Aβ by β-secretase activity. The inhibition of BACE-1 has been shown to inhibit the production of Aβ.

AD is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and gamma-secretase activity, can form tertiary structures that aggregate to form amyloid fibrils. Aβ peptides have also been shown to form Aβ oligomers (sometimes referred to as "Aβ aggregates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ, Aβ fibrils, aggregates, oligomers, and/or plaque play a causal role in AD pathophysiology. (Ohno et al., Neurobiology of Disease, No. 26 (2007), 134-145). Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuronal cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., J. Bio. Chem., Vol. 282, No. 36 (September 2007), have shown that partial reductions of BACE-1 enzyme activity and concomitant reductions of Aβ levels lead to a dramatic inhibition of Aβ-driven AD-like pathology, making β-secretase a target for therapeutic intervention in AD. Ohno et al. Neurobiology of Disease, No. 26 (2007), 134-145, report that genetic deletion of BACE-1 in 5XFAD mice abrogates Aβ generation, blocks amyloid deposition, prevents neuron loss found in the cerebral cortex and subiculum (brain regions manifesting the most severe amyloidosis in 5XFAD mice), and rescues memory deficits in 5XFAD mice. The group also reports that Aβ is ultimately responsible for neuron death in AD and concludes that BACE-1 inhibition has been validated as an approach for the treatment of AD. Roberds et al., Human Mol. Genetics, 2001, Vol. 10, No. 12, 1317-1324, established that inhibition or loss of β-secretase activity produces no profound phenotypic defects while inducing a concomitant reduction in Aβ. Luo et al., Nature Neuroscience, Vol. 4, No. 3, March 2001, report that mice deficient in BACE-1 have normal phenotype and abolished β-amyloid generation.

More recently, Jonsson, et al. have reported in Nature, Vol. 488, pp. 96-99 (August 2012), that a coding mutation (A673T) in aPP gene protects against Alzheimer's disease and cognitive decline in the elderly without Alzheimer's disease. More specifically, an allele of rs63750847, a single nucleotide polymorphism (SNP), results in an alanine to threonine substitution at position 673 in APP (A673T). This SNP was found to be significantly more common in a healthy elderly control group than in an Alzheimer's disease group. A673T substitution is adjacent to aspartyl protease beta-site in APP, and results in an approximately 40% reduction in the formation of amyloidogenic peptides in a heterologous cell expression system in vitro. Jonsson, et al. report that an APP-derived peptide substrate containing a673T mutation is processed 50% less efficiently by purified human BACE-1 enzyme when compared to a wild-type peptide. Jonsson et al. indicate that the strong protective effect of aPP-A673T substitution against Alzheimer's disease provides proof of principle for the hypothesis that reducing the beta-cleavage of APP may protect against the disease.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of aPP gene found in these patients, which leads to overexpression of APP and therefore to increased levels of Aβ causing the prevalence of AD seen in this population. Furthermore, Down's patients who have a duplication of a small region of chromosome 21 that does not include aPP gene do not develop AD pathology. Thus, it is thought that inhibitors of BACE-1 could be useful in reducing Alzheimer's type pathology in Down's syndrome patients.

Another example is in the treatment of glaucoma (Guo et al., PNAS, Vol. 104, No. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., Neurobiology of Aging, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., Ann NY Acad Sci 2002; 855:723-31; Crino P B, Martin J A, Hill W D, et al., Ann Otol Rhinol Laryngol, 1995; 104:655-61; Davies D C, et al., Neurobiol Aging, 1993; 14:353-7; Devanand D P, et al., Am J Psychiatr, 2000; 157:1399-405; and Doty R L, et al., Brain Res Bull, 1987; 18:597-600. It is reasonable to suggest that addressing such changes by reduction of Aβ by inhibition of BACE-1 could help to restore olfactory sensitivity in patients with AD.

For compounds which are inhibitors of BACE-2, another example is in the treatment of type-II diabetes, including diabetes associated with amyloidogenesis. BACE-2 is expressed in the pancreas. BACE-2 immunoreactivity has been reported in secretory granules of beta cells, co-stored with insulin and IAPP, but lacking in the other endocrine and exocrine cell types. Stoffel et al., WO2010/063718, disclose the use of BACE-2 inhibitors in the treatment of metabolic diseases such as Type-II diabetes. The presence of BACE-2 in secretory granules of beta cells suggests that it may play a role in diabetes-associated amyloidogenesis. (Finzi, G. Franzi, et al., Ultrastruct Pathol. 2008 November-December; 32(6):246-51.)

Other diverse pathologies characterized by the formation and deposition of Aβ or fragments thereof, and/or by the presence of amyloid fibrils, oligomers, and/or plaques, include neurodegenerative diseases such as scrapie, bovine spongiform encephalitis, traumatic brain injury ("TBI"), Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. As another example, Loane, et al. report the targeting of amyloid precursor protein secretases as therapeutic targets for traumatic brain injury. (Loane et al., "Amyloid precursor protein secretases as therapeutic targets for traumatic brain injury", Nature Medicine, Advance Online Publication, published online Mar. 15, 2009.) Still other diverse pathologies characterized by the inappropriate formation and deposition of Aβ or fragments thereof, and/or by the presence of amyloid fibrils, and/or for which inhibitor(s) of BACE are expected to be of therapeutic value are discussed further hereinbelow.

The compound:

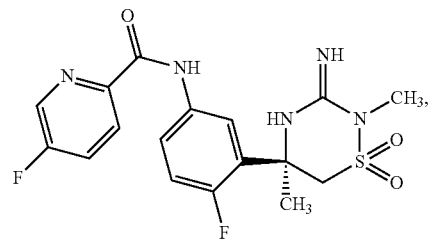 [SMILES: CN1C(=N)N[C@](C)(c2cc(NC(=O)c3ccc(F)cn3)ccc2F)CS1(=O)=O]

and its tautomer:

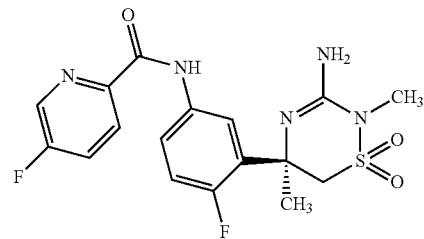 [SMILES: CN1C(N)=N[C@](C)(c2cc(NC(=O)c3ccc(F)cn3)ccc2F)CS1(=O)=O]

which are collectively and individually referred to herein as "verubecestat", and pharmaceutically acceptable salts thereof, are disclosed in U.S. Pat. No. 8,729,071, PCT Patent Publication No. WO2011/044181 (incorporated herein by reference), as a potent inhibitor of BACE-1 and BACE-2, together with pharmaceutical compositions thereof. Also disclosed is the use of verubecestat in treating, preventing, ameliorating, and/or delaying the onset of an Aβ pathology and/or a symptom or symptoms thereof, including Alzheimer's disease. A preparation of verubecestat is also disclosed therein.

The "endo" (or "amine") tautomer of verubecestat may be depicted as

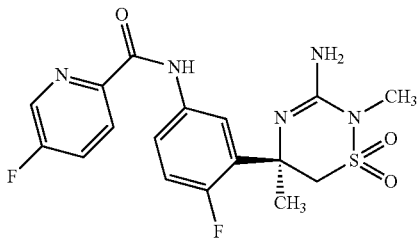 [SMILES: CN1C(N)=N[C@](C)(c2cc(NC(=O)c3ccc(F)cn3)ccc2F)CS1(=O)=O]

and named as N-[3-[(5R)-3-amino-5,6-dihydro-2,5-dimethyl-1,1-dioxido-2H-1,2,4-thiadiazin-5-yl]-4-fluorophenyl]-5-fluoro-2-pyridinecarboxamide.

The "exo" (or "imine") tautomer of verubecestat may be depicted as

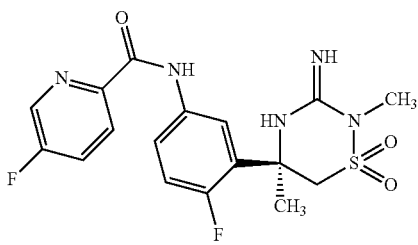 [SMILES: CN1C(=N)N[C@](C)(c2cc(NC(=O)c3ccc(F)cn3)ccc2F)CS1(=O)=O]

and named as 5-fluoro-N-[4-fluoro-3-[(5R)-tetrahydro-3-imino-2,5-dimethyl-1,1-dioxido-2H-1,2,4-thiadiazin-5-yl]phenyl]-2-pyridinecarboxamide.

The physical and biological attributes of a drug's active ingredient, such as solubility, stability, melting point, bioavailability, and the like can be affected by the solid-state form. There remains a need in art to identify a suitable solid-state form of verubecestat which may be beneficial to achieving acceptable biological and physical properties while minimizing difficulties with drug substance manufacturing, processing, and storage. The present invention relates to this need.

SUMMARY OF THE INVENTION

In its many embodiments, the present invention provides two novel crystalline forms of verubecestat, and two novel crystalline forms of the tosylate salt of verubecestat, as well as pharmaceutically acceptable compositions thereof, each of which may be useful (alone or together with additional active ingredients) in treating, preventing, ameliorating, and/or delaying the onset of an Aβ pathology and/or a symptom or symptoms thereof. Non-limiting examples of such Aβ pathologies, including Alzheimer's disease, are disclosed herein.

DETAILED DESCRIPTION OF THE INVENTION

Definitions

Figure 1:
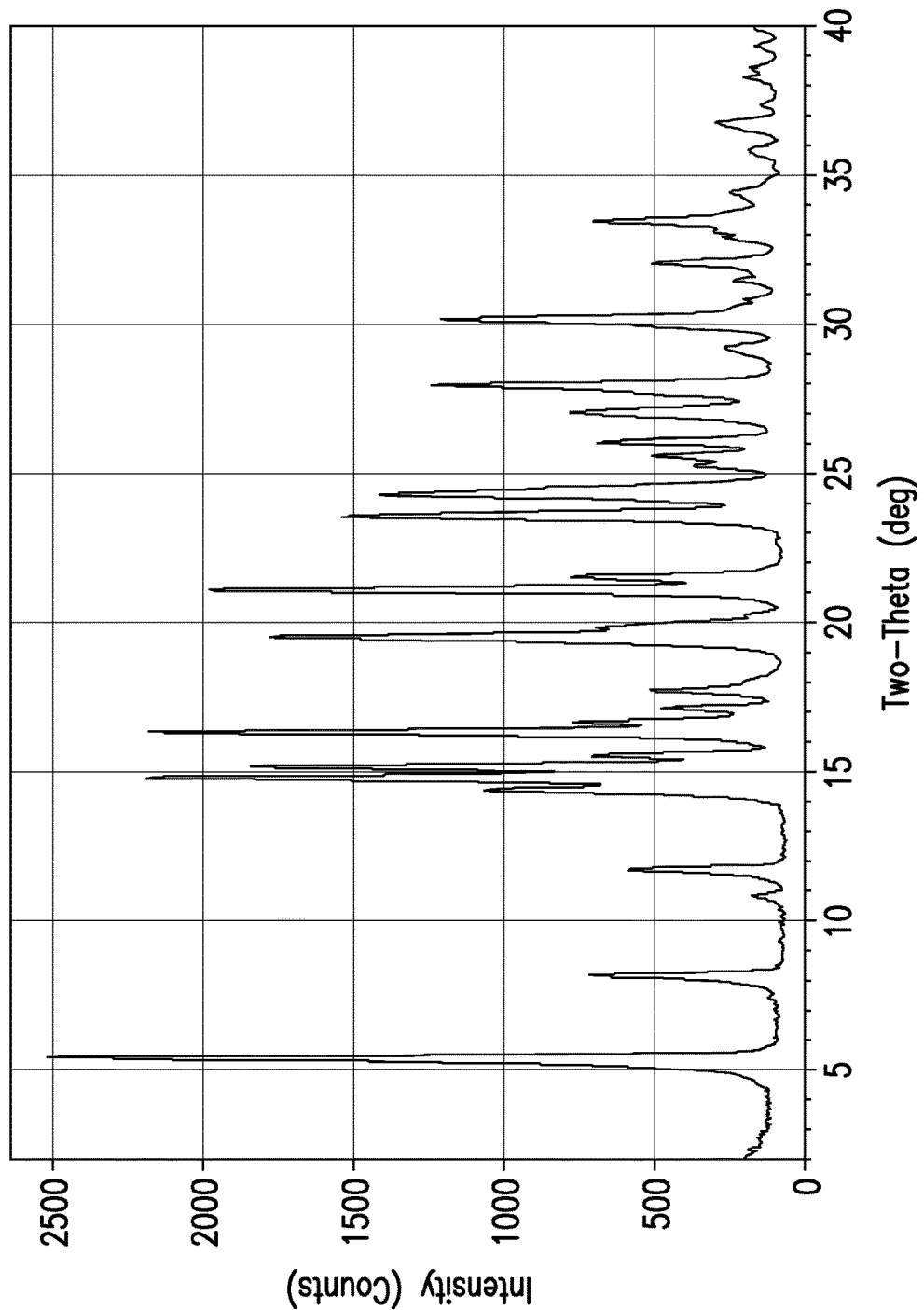
FIG. 1 is a graph of a Powder X-Ray Diffraction ("PXRD") pattern of Crystalline Tosylate Form 2 of Verubecestat, generated using the equipment and methods described herein. The graph plots the intensity of the peaks as defined by counts per second versus the diffraction angle 2Θ (2 theta) in degrees.

The terms used herein have their ordinary meaning and the meaning of such terms is independent at each occurrence thereof. That notwithstanding and except where stated otherwise, the following definitions apply throughout the specification and claims.

"FIG" means "Figure" (or "figure") and refers to the corresponding drawing.

"Patient" includes both human and other animals.

"Mammal" includes humans and other mammalian animals.

"m/z" refers to a mass spectrum peak.

"XRPD" refers to powder x-ray diffraction.

"DSC" refers to differential scanning calorimetry.

"TGA" refers to thermal gravimetric analysis.

"Excipient" means an essentially inert substance used as a diluent or to give form or consistency to a formulation.

The term "composition" (or "pharmaceutical composition" or "pharmaceutically acceptable composition") as used herein is intended to encompass a product comprising the specified ingredients in the specified amounts, as well as any product which results, directly or indirectly, from combining the specified ingredients in the specified amounts. The term is intended to encompass a product comprising active ingredient(s), and the inert ingredient(s), if any, that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the invention encompass any composition made by admixing a crystalline form according to the invention and a pharmaceutically acceptable carrier. By "pharmaceutically acceptable" it is meant the carrier, diluent or excipient must be compatible with the other ingredients of the formulation and not deleterious to the recipient thereof.

The term "composition" (or "pharmaceutical composition" or "pharmaceutically acceptable composition") as used herein is also intended to encompass either the bulk composition and/or individual dosage units. (Such compositions and units can additionally comprise additional active ingredients as described herein.) The bulk composition and each individual dosage unit can contain fixed amounts of active agent(s). The bulk composition is material that has not yet been formed into individual dosage units. Non-limiting examples of dosage units include oral dosage units such as tablets, pills and the like. Similarly, the herein-described method of treating a patient by administering a pharmaceutical composition of the present invention is also intended to encompass administration of afore-said bulk composition and individual dosage units.

As noted above, verubecestat is capable of tautomerism and may therefore be depicted as the "endo" (or "amine") form or the "exo" (or "imine") form, each of which are shown above. For ease of description, and unless otherwise specified, the structural formula:

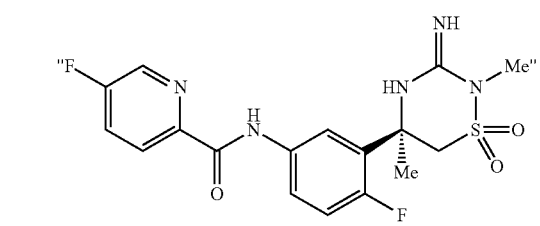

is intended to encompass the endo form, or the exo form, or a mixture of both of the endo and exo forms. Those skilled in the art will appreciate that the relative amount(s) of each tautomeric form of verubecestat that is (or is not) present in a given sample may vary as influenced by the physical conditions in which the sample is present.

Synthesis of Verubecestat

This patent application discloses novel crystalline forms of verubecestat as described herein. As noted above, a synthesis for the preparation of verubecestat is disclosed in WO2011/044181. Another novel synthesis is described in Applicant's patent application entitled "Process for the Preparation of a BACE inhibitor", U.S. Provisional Patent Application Nos. 62/037,423, filed Aug. 14, 2014, and 62/182,117, filed Jun. 19, 2015, and in PCT application No. PCT/US15/044410, filed Aug. 10, 2015. Another synthesis of verubecestat (the Compound of Formula (I)), as well as synthetic intermediates which are useful in, among other things, the preparation of the Compound of the Formula (I), which is described in Applicant's International Patent Application No. PCT/US15/044418, filed Aug. 10, 2015, may be described as follows.

General Scheme A

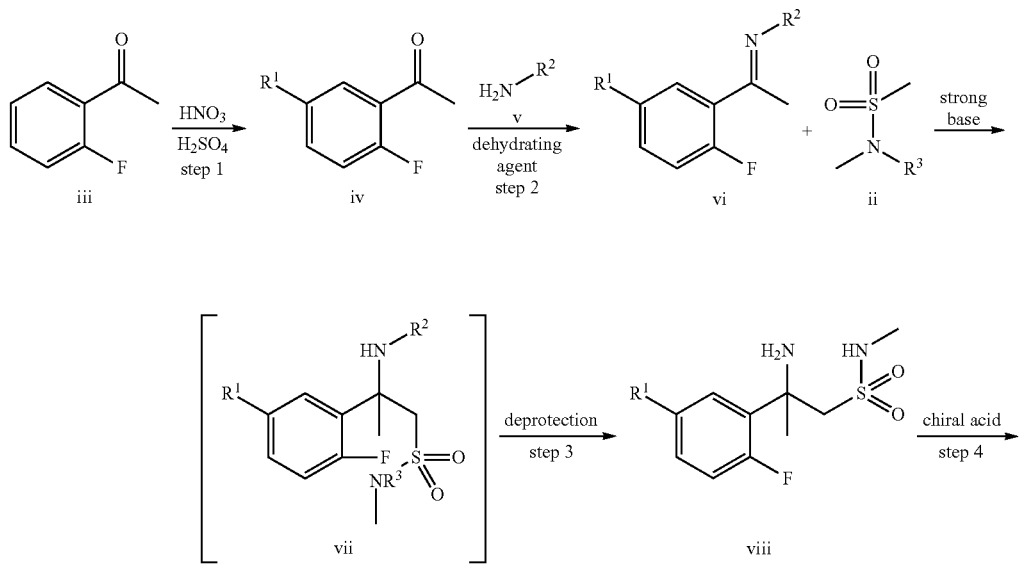

-continued

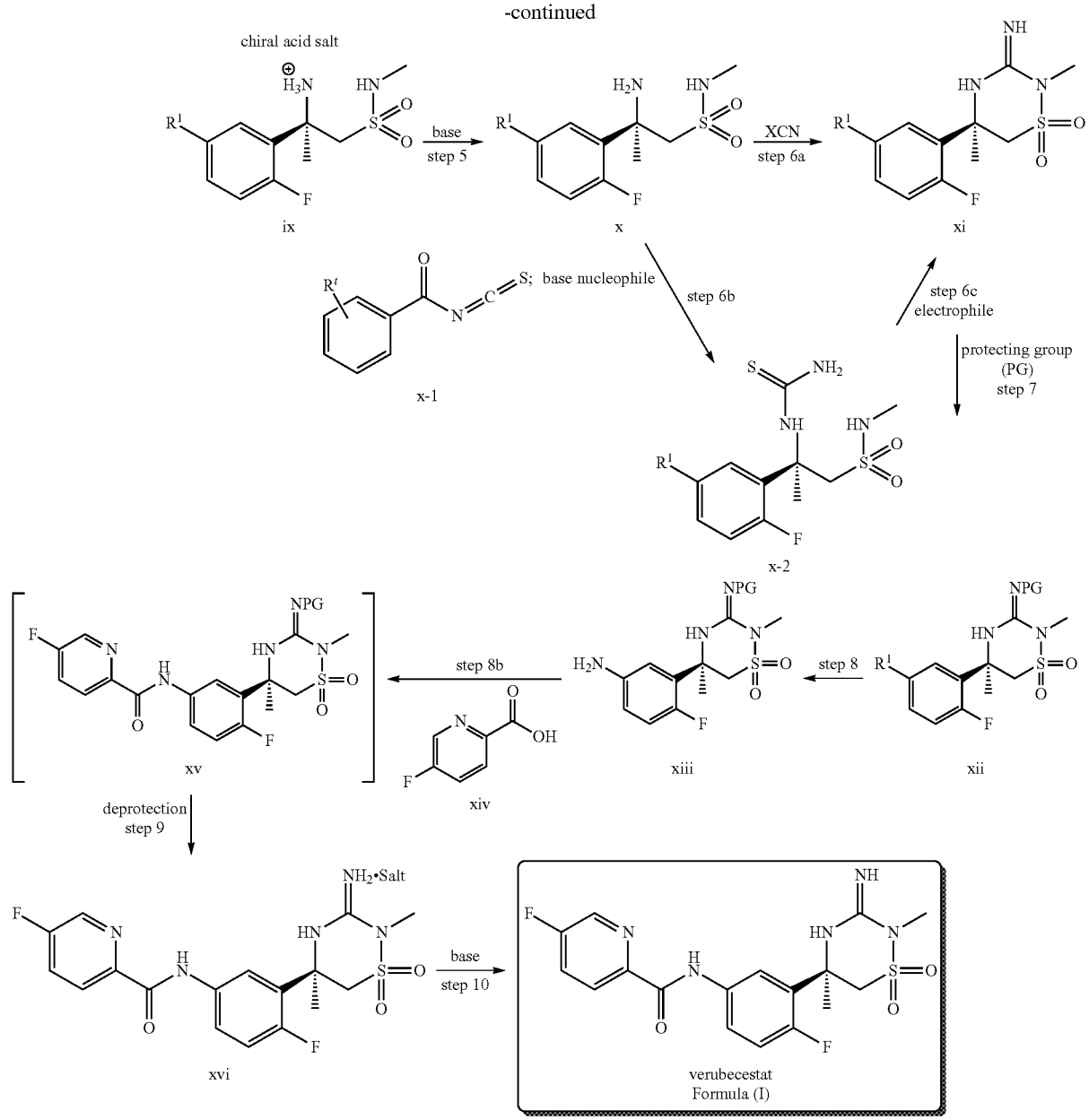

As shown in General Scheme A, step 10, the compound of Formula (I) may be prepared from the corresponding salt, depicted as compound xvi having a formula:

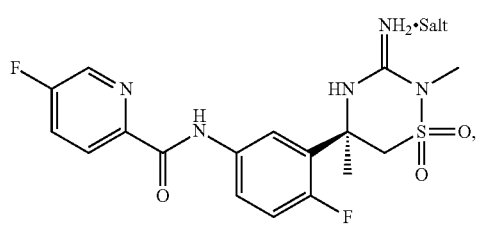

wherein Salt is any suitable salt, by the addition of a suitable base, optionally in the presence of a solvent. Suitable salts include fluoride, chloride, bromide, iodide, tetrafluoroborate, mesylate, tosylate, triflate, sulfate, bisulfate, nitrate, trifluoroacetate, perchlorate, and the like. In one embodiment, the Salt is the tosylate salt of compound xvi. Suitable bases include lithium carbonate, sodium carbonate, potassium carbonate, sodium bicarbonate, potassium bicarbonate, sodium phosphate monobasic, sodium phosphate dibasic, sodium phosphate tribasic, potassium phosphate monobasic, potassium phosphate dibasic, potassium phosphate tribasic, lithium hydroxide, sodium hydroxide, potassium hydroxides, sodium borate, potassium borate, sodium methoxide, potassium methoxide, sodium tert-butoxide, potassium tert-butoxide, triethyl amine, diisopropylethyl amine, pyridine, methylamine, ethylamine, dibenzylamine, diisopropylamine, and pyridine. In one such embodiment, the base is potassium carbonate. Suitable solvents include water and/or a suitable organic solvent. Non-limiting examples of suitable organic solvents include ethylacetate, heptane, isopropyl acetate, isobutyl acetate, n-butyl acetate, acetone, methyl ethyl ketone, methanol, isopropanol, n-butanol, tetrahydrofuran, 2-methyltetrahydrofuran, methyl tertiarybutyl ether, dichloromethane, 1,2-dichloroethane, toluene, xylenes, ethyl benzene, and acetonitrile. In one such embodiment, the solvents are water and ethyl acetate.

As shown in General Scheme A, step 9, the compound xvi may be prepared by deprotecting compound xv, having a formula:

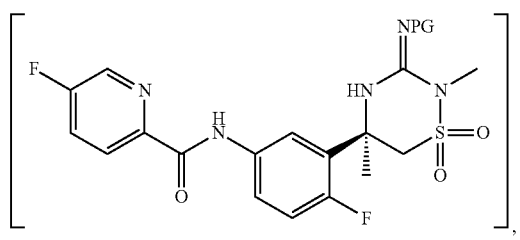
xv wherein "PG" is a suitable protecting group. Deprotection may be achieved by treating compound xv with a suitable Lewis or a Brønsted Acid. Non-limiting examples of PG include —S(O)$_2$R$^8$, —C(O)OR$^8$, —C(O)R$^8$, —CH$_2$OCH$_2$CH$_2$SiR$^8$, and R$_8$, where R$^8$ is independently selected from the group consisting of —C$_{1-8}$ alkyl (straight or branched), —C$_{3-8}$ cycloalkyl, aryl, —CH$_2$(aryl), and —CH(aryl)$_2$, wherein each aryl is independently phenyl or naphthyl and optionally substituted with one or more (e.g., 1, 2, or 3) groups independently selected from —OMe, Cl, Br, and I. In one embodiment, the PG is tert-butyl carbamate (Boc). Suitable Lewis or Brønsted acids include hydrochloric acid, hydrobromic acid, hydrofluoric acid, hydroiodic acid, sulfuric acid, acetic acid, trifluoroacetic acid, methansulfonic acid, trifluoromethanesulfonic acid, tetrafluoroboric acid, aluminum trichloride, boron trifluoride, and para-toluenesulfonic acid. In one such embodiment, the acid is para-toluenesulfonic acid.

As shown in General Scheme A, step 8b, compound xv is prepared by amide coupling of a compound xiv having a formula:

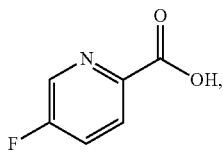
xiv with a compound xiii having a formula:

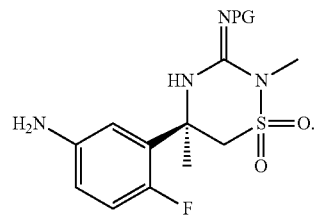
xiii

Suitable amide coupling reagents include T3P™ (1-propanephosphonic anhydride solution), EDC (1-Ethyl-3-(3-dimethylaminopropyl)carbodiimide), and HATU (1-Bis(dimethylamino)methylene]-1H-1,2,3-triazol[4,5-b]pyridinium 3-oxide hexafluorophosphate). In one embodiment, the amide coupling agent is T3P™.

In General Scheme A, step 8, compound xiii may be prepared by a one step or a two step process from a compound xii having a formula:

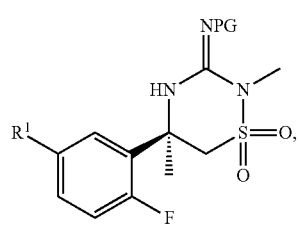
xii wherein PG is a protecting group as described above. In the one step process, R$^1$ of compound xii is nitro. In this one step process, compound xii is reduced by any suitable method such as hydrogenation or zero-valent metal reduction. Suitable reducing conditions include palladium on carbon and hydrogen gas. As an alternative one step process, R$^1$ in compound xii is Cl, Br, I, tosylate, mesylate, or triflate. In this alternative one step process, compound xii is aminated in the presence ammonia or a suitable ammonium salt such as NH$_4$OAc or (NH$_4$)$_2$SO$_4$ and a suitable nickel or palladium catalyst. See Hartwig et al. Angewandte Chemie International Edition 2015, 54, 3768-3772. When compound xiii in General Scheme A, step 8, is prepared according to a two step process, R$^1$ in compound xii is selected from Cl, Br, I, mesylate, triflate and tosylate. In this two step process, compound xii is 1) nitrated, and then 2) reduced by any suitable method such as hydrogenation or zero-valent metal reduction. For nitration, See Buchwald et al., J. Am. Chem. Soc., 2009, 131 (36), pp 12898-12899.

As shown in General Scheme A, step 7, compound xii may be prepared by protecting a compound xi having a formula:

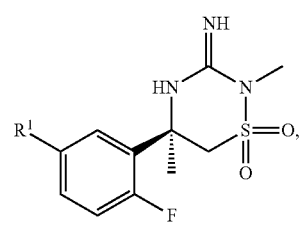
xi wherein R¹ is nitro, Cl, Br, I, or OH, with a suitable protecting group (PG). Non-limiting protecting groups (PG) include, —S(O)₂R⁸, —C(O)OR⁸, —C(O)R⁸, —CH₂OCH₂CH₂SiR⁸, and CH₂R₈ where R⁸ is independently selected from the group consisting of $C_{1-8}$ alkyl (straight or branched), $C_{3-8}$ cycloalkyl, CH₂(aryl), and CH(aryl)₂, wherein each aryl is independently phenyl or naphthyl and optionally substituted with H, OMe, Cl, Br, I and the like. In one embodiment, the PG is tert-butyl carbamate (Boc).

As shown in General Scheme A, step 6a, compound xi may be prepared from a compound x having a formula:

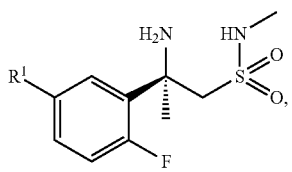

wherein R¹ is nitro, Cl, Br, I, or OH, in a single step cyclization reaction in the presence of a cyanating reagent ("XCN"). Suitable cyanating reagents include cyanogen, cyanogen bromide, cyanogen fluoride, cyanogen chloride, cyanogen iodide, 2-methoxyphenyl cyanate, 4-methoxyphenyl cyanate, 4-phenylphenyl cyanate, and bisphenol A cyanate. In one such embodiment, the cyanating agent is cyanogen bromide.

Alternatively, as shown in General Scheme A, compound xi may be prepared in two steps as shown in step 6b and step 6c. In step 6c, compound xi may be prepared by cyclizing a compound x-2, having a formula:

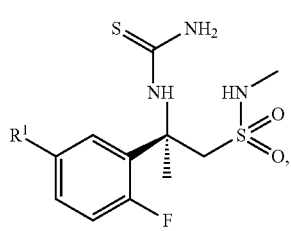

wherein R¹ is nitro, Cl, Br, I, or OH, with an electrophile in the presence of a solvent to form compound xi. Suitable electrophiles include any straight C1-C6 alkyl iodide or branched C3-C6 alkyl iodide. Suitable solvents include any organic solvent known to those skilled in the art. In one such embodiment, the electrophile is methyl iodide and the solvent is ethanol.

As shown in step 6b of General Scheme A, the compound x-2 may be prepared by reacting a compound x having the formula:

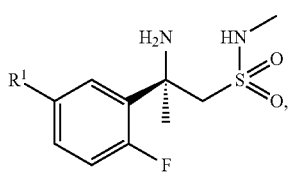

wherein R¹ is nitro, Cl, Br, I, or OH, with a benzothiocarbimide compound x-1, having a formula:

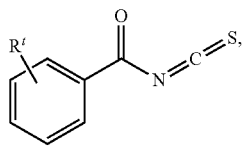

wherein R' is 1-2 substituents independently selected from the group consisting of from H, halo, nitro, straight $C_1$-$C_6$ alkyl, branched $C_3$-$C_6$ alkyl, straight $C_1$-$C_6$ alkoxy, and branched $C_3$-$C_6$ alkoxy, followed by treatment with a base and nucleophile to generate the corresponding thiourea compound x-2. Suitable bases include lithium carbonate, sodium carbonate, potassium carbonate, sodium bicarbonate, potassium bicarbonate, sodium phosphate monobasic, sodium phosphate dibasic, sodium phosphate tribasic, potassium phosphate monobasic, potassium phosphate dibasic, potassium phosphate tribasic, potassium tert-butoxide, lithium hydroxide, sodium hydroxide, potassium hydroxides, sodium borate, potassium borate, triethyl amine, diisopropylethyl amine, pyridine, dibenzylamine, and diisopropylamine. Suitable nucleophiles include straight $C_1$-$C_6$ alcohol, branched C3-C6 alcohol, straight $C_1$-$C_6$ alkyl amine, or branched $C_3$-$C_6$ alkyl amine. In one embodiment, R' of compound x-1 is H, the base is sodium carbonate, and the nucleophile is methanol.

As shown in General Scheme A, step 5, compound x, may be prepared by treating a chiral acid salt, compound ix, having a formula:

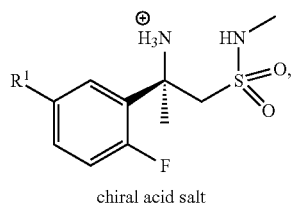

chiral acid salt wherein R¹ is nitro, Cl, Br, I, or OH, in the presence of a suitable solvent and a suitable base. Suitable solvents include water and one or more organic solvents such as ethylacetate, heptane, isopropyl acetate, isobutyl acetate, n-butyl acetate, acetone, methyl ethyl ketone, methanol, isopropanol, n-butanol, tetrahydrofuran, 2-methyltetrahydrofuran, methyl tertiarybutyl ether, dichloromethane, 1,2-dichloroethane, toluene, xylenes, ethyl benzene, and acetonitrile. In one such embodiment, the solvents are water and isopropyl acetate. Suitable bases include lithium carbonate, sodium carbonate, potassium carbonate, sodium bicarbonate, potassium bicarbonate, sodium phosphate monobasic, sodium phosphate dibasic, sodium phosphate tribasic, potassium phosphate monobasic, potassium phosphate dibasic, potassium phosphate tribasic, lithium hydroxide, sodium hydroxide, potassium hydroxides, sodium borate, potassium borate, sodium methoxide, potassium methoxide, sodium tert-butoxide, potassium tert-butoxide, triethyl amine, diisopropylethyl amine, pyridine, methylamine, ethylamine, dibenzylamine, diisopropylamine, and pyridine. In one such embodiment, the base is sodium carbonate.

As shown in General Scheme A, step 4, the chiral acid salt, compound ix, is prepared by treating a compound viii, having a formula:

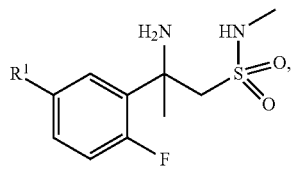

viii wherein $R^1$ is nitro, Cl, Br, I, or OH with a chiral acid in the presence of a solvent. When $R^1$ of compound viii is nitro, the chiral acid is L-mandelic acid. When $R^1$ of compound viii is Cl, Br, I, tosylate, mesylate, or triflate, the chiral acid is selected from L-mandelic acid, L-aspartic acid, Camphor sulfonic acid, (R)-1,4-Benzodioxane-2-carboxylic acid, N,N-Bis[(R)-(+)-1-phenylethyl]phthalamic acid, (1S)-(+)-3-Bromocamphor-10-sulfonic acid, (1R)-(+)-Camphanic acid, (1R,3S)-(+)-Camphoric acid, (+)-2,3-Dibenzoyl-D-tartaric acid, (−)-O,O'-Di-p-toluoyl-L-tartaric acid, D-glutamic acid, L-(−)-Malic acid, (−)-Menthyloxyacetic acid, (R)-(−)-α-Methoxyphenylacetic acid, (R)-(+)-α-Methoxy-α-trifluoromethylphenyl acetic acid, (R)-(+)-N-[1-(1-Naphthyl)ethyl]succinamic acid, (R)-(−)-5-Oxo-2-tetrahydrofurancarboxylic acid, (R)-(+)-N-(1-Phenylethyl)phthalamic acid, (R)-(+)-N-(1-Phenylethyl)succinamic acid, (R)-(−)-2-Phenylpropionic acid, L-Pyroglutamic acid, D-(−)-Quinic acid, D-(−)-Tartaric acid, L-Valine, and the enatiomers thereof. In one such embodiment the chiral acid is selected from: L-Mandelic acid, Camphor sulfonic acid, (R)-1,4-Benzodioxane-2-carboxylic acid, N,N-Bis[(R)-(+)-1-phenylethyl]phthalamic acid, (1S)-(+)-3-Bromocamphor-10-sulfonic acid, (1R)-(+)-Camphanic acid, (1R,3S)-(+)-Camphoric acid, (+)-2,3-Dibenzoyl-D-tartaric acid, (−)-O,O'-Di-p-toluoyl-L-tartaric acid, D-glutamic acid, L-(−)-Malic acid, (R)-(−)-α-Methoxyphenylacetic acid, (R)-(+)-α-Methoxy-α-trifluoromethylphenylacetic acid, (R)-(+)-N-[1-(1-Naphthyl)ethyl]succinamic acid, (R)-(−)-5-Oxo-2-tetrahydrofurancarboxylic acid, (R)-(+)-N-(1-Phenylethyl)phthalamic acid, (R)-(+)-N-(1-Phenylethyl)succinamic acid, (R)-(−)-2-Phenylpropionic acid, L-Pyroglutamic acid, D-(−)-Quinic acid, D-H-Tartaric acid, L-Valine and the enantiomers thereof. In one such embodiment, the chiral acid is L-Mandelic Acid. Suitable solvents include water and any commercially available organic solvent. In one such embodiment, suitable solvents include ethylacetate, heptane, isopropyl acetate, isobutyl acetate, n-butyl acetate, acetone, methyl ethyl ketone, methanol, isopropanol, n-butanol, tetrahydrofuran, 2-methyltetrahydrofuran, methyl tertiarybutyl ether, dichloromethane, 1,2-dichloroethane, toluene, xylenes, ethyl benzene, water and acetonitrile. In one such embodiment, the solvent is acetonitrile.

As shown in General Scheme A, step 3, compound viii is prepared by deprotecting a compound vii, having a formula:

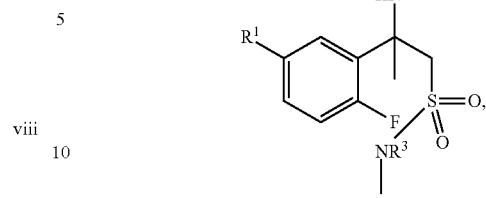

vii wherein $R^1$ is nitro, Cl, Br, or I; and $R^2$ is —S(O)$C_1$-$C_6$ alkyl; or —S(O)phenyl, wherein said phenyl is unsubstituted or substituted with from 1 to 3 substituents independently selected from the group consisting of $C_1$-$C_4$ alkyl, $C_1$-$C_4$ haloalkyl, —O—$C_1$-$C_4$ alkyl, —O—$C_1$-$C_4$ haloalkyl, halo, and nitro; and $R^3$ is an alkyl protecting group. In one embodiment, the alkyl protecting group is PMB (paramethoxybenzyl) Suitable deprotecting reagents include trifluoroacetic acid, hydrochloric acid, sulfuric acid, hydrobromic acid (HBr), methanesulfonic acid, tetrafluoroboric acid, trifluoromethanesulfonic acid, fumaric acid, and citric acid. In one such embodiment, the acid is trifluoroacetic acid (TFA). Compound vii may be prepared according Scheme 1 and the detailed steps 1 to 3, described below. A non-limiting example synthesis of Compound of Formula (I) is described in the following Schemes and Steps.

Scheme 1

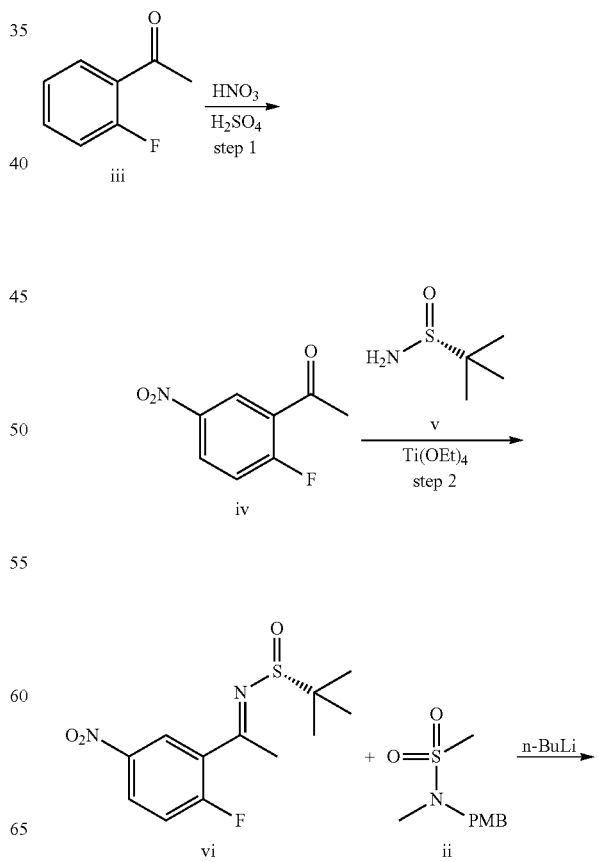

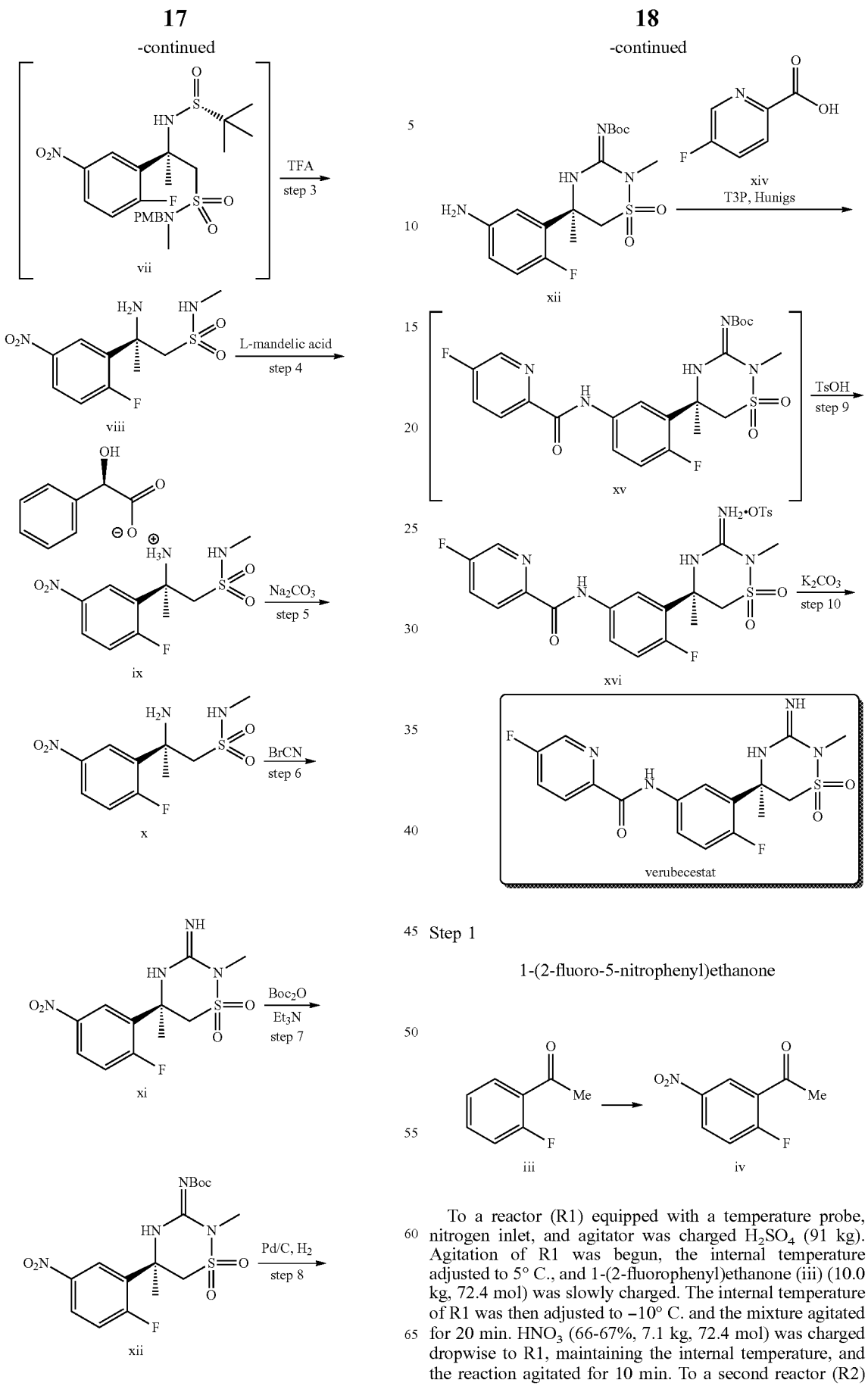

Step 1

1-(2-fluoro-5-nitrophenyl)ethanone

To a reactor (R1) equipped with a temperature probe, nitrogen inlet, and agitator was charged H₂SO₄ (91 kg). Agitation of R1 was begun, the internal temperature adjusted to 5° C., and 1-(2-fluorophenyl)ethanone (iii) (10.0 kg, 72.4 mol) was slowly charged. The internal temperature of R1 was then adjusted to −10° C. and the mixture agitated for 20 min. HNO₃ (66-67%, 7.1 kg, 72.4 mol) was charged dropwise to R1, maintaining the internal temperature, and the reaction agitated for 10 min. To a second reactor (R2)

equipped with a temperature probe, nitrogen inlet, and agitator was charged water (300 kg). Agitation of R2 was begun and the internal temperature adjusted to 5° C., at which point the reaction mixture from R1 was transferred to R2, maintaining the internal temperature. The mixture was stirred for 2 h and the resulting solids were collected and washed with water (40 kg) to provide 1-(2-fluoro-5-nitrophenyl)ethanone (iv) (10.8 kg).

Step 2

(R,E)-N-(1-(2-fluoro-5-nitrophenyl)ethylidene)-2-methylpropane-2-sulfinamide

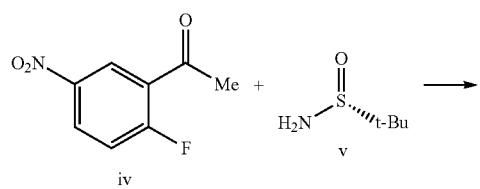

To a reactor (R1) equipped with a temperature probe, nitrogen inlet, and agitator was charged EtOAc (340 kg) followed by 1-(2-fluoro-5-nitrophenyl)ethanone (iv) (60.0 kg, 327.9 mol) and (R)-2-methylpropane-2-sulfinamide (v) (47.8 kg, 393.5 mol). Agitation of R1 was begun and to this mixture was charged Ti(Oet)$_4$ (164.8 kg, 721.4 mol). R1 was degassed and purged with N$_2$ twice, the internal temperature adjusted to 55° C., and the reaction was stirred for 18 h. When the reaction was judged complete, the internal temperature was adjusted to 25° C. To a second reactor (R2) equipped with a temperature probe, nitrogen inlet, and agitator was charged 7% aqueous NaHCO$_3$ (610 kg). Agitation of R2 was begun, the internal temperature adjusted to 5° C., and then the contents of R1 transferred to R2; R1 was rinsed with EtOAc (140 kg). R2 was agitated for 1 h and the resulting mixture centrifuged using EtOAc (852 kg) to slurry the wet cake. The filtrate was transferred to R1 and agitated for 20 min before the layers were allowed to separate. The organic layer was retained in R1 and the aqueous layer transferred to R2. R2 was then charged with EtOAc (276 kg), the contents agitated, the layers allowed to separated, and the organic layer transferred to R1. To R1 was charged 5% aqueous NaCl (470 kg) and the resulting mixture agitated for 30 min before the layers were allowed to separate. The organic layer was transferred to a third reactor (R3) and concentrated to approximately 690 L. EtOAc (360 kg) was charged and the contents concentrated to approximately 690 L; this process was repeated until the amount of residual water and EtOH were judged to be satisfactory. Activated carbon (17.4 kg) was charged into R3, the internal temperature adjusted to 25° C., and the resulting mixture agitated for 4 h. The slurry was filtered through diatomaceous earth into a fourth reactor (R4) equipped with a temperature probe, nitrogen inlet, and agitator; the filter was washed with EtOAc (84 kg). Agitation of R4 was begun and the solution concentrated to approximately 150 L and then slowly cooled to 25° C. At this point heptane (409 kg) was added dropwise and the solution concentrated to approximately to 480 L. The resulting solids were collected, washed with heptane (65 kg), and dried to provide (R,E)-N-(1-(2-fluoro-5-nitrophenyl)ethylidene)-2-methylpropane-2-sulfinamide (vi) (66.2 kg).

Step 3

(R)-2-amino-2-(2-fluoro-5-nitrophenyl)-N-methylpropane-1-sulfonamide

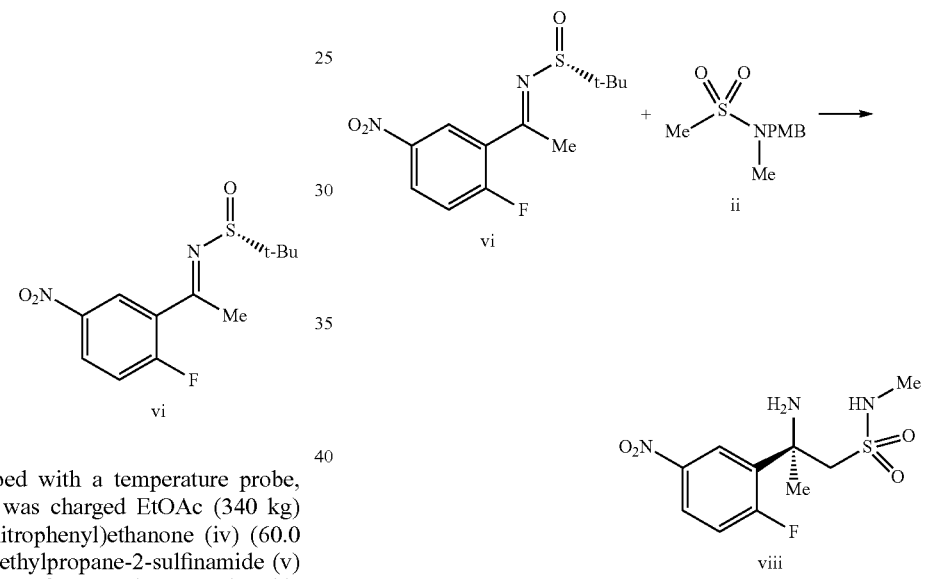

To a reactor (R1) equipped with a temperature probe, nitrogen inlet, and agitator was charged THF (350 kg) followed by N-(4-methoxybenzyl)-N-methylmethanesulfonamide (ii), obtained by Step A above, (69 kg, 279.4 mol). Agitation of R1 was begun, the internal temperature adjusted to −60° C., and then n-BuLi (77 kg, 279.4 kg) was charged over 1.5 h, maintaining the internal temperature below −40° C. The resulting mixture was agitated for 1 h. To a second reactor (R2) equipped with a temperature probe, nitrogen inlet, and agitator was charged THF (201 kg) followed by (R,E)-N-(1-(2-fluoro-5-nitrophenyl)ethylidene)-2-methylpropane-2-sulfinamide (vi) (45.5 kg, 139.7 mol). Agitation of R2 was begun, the internal temperature adjusted to −60° C., and then the contents transferred to R1. R1 was agitated for 1 h and then trifluoroacetic acid was charged to R1, maintaining the internal temperature below −50° C. After the addition was complete, the internal temperature of R1 was adjusted to 23° C. to provide (R)-2-amino-2-(2-fluoro-5-nitrophenyl)-N-methylpropane-1-sulfonamide (viii) (51.6 kg) which was used directly in the next step without purification.

Step 4

(R)-2-(2-fluoro-5-nitrophenyl)-1-(N-methylsulfamoyl)propan-2-aminium (R)-2-hydroxy-2-phenylacetate

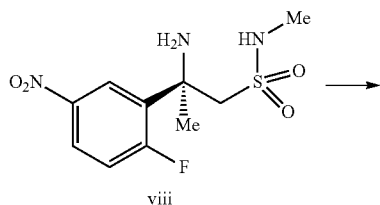

viii

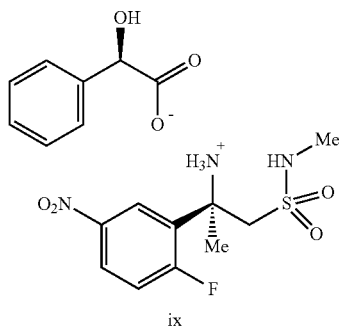

ix

To a reactor (R1) equipped with a temperature probe, nitrogen inlet, and agitator was charged (R)-2-amino-2-(2-fluoro-5-nitrophenyl)-N-methylpropane-1-sulfonamide (viii) (189.9 kg, 581 mol) and MeCN (841 kg). Agitation of R1 was begun and the internal temperature adjusted to 50-60° C. and maintained at that temperature for 12-20 min. A solution of L-mandelic acid (118.6 kg, 698 mol) in MeCN (950 kg) was then added dropwise over 10 h. The internal temperature was adjusted to 20-30° C. and the contents concentrated to approximately 3-5 volumes before being cooled to 8-11° C. for 5-8 h and the solids collected to provide (R)-2-(2-fluoro-5-nitrophenyl)-1-(N-methylsulfamoyl)propan-2-aminium (R)-2-hydroxy-2-phenylacetate (ix) (226.8 kg).

Step 5

(R)-2-amino-2-(2-fluoro-5-nitrophenyl)-N-methylpropane-1-sulfonamide

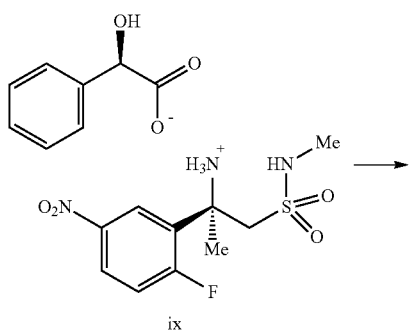

ix

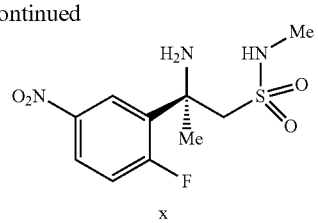

x

To a reactor (R1) equipped with a temperature probe, nitrogen inlet, and agitator was charged (R)-2-(2-fluoro-5-nitrophenyl)-1-(N-methylsulfamoyl)propan-2-aminium (R)-2-hydroxy-2-phenylacetate (ix) (112.6 kg, 253.9 mol), water (540 kg) and i-PrOAc (1892 kg). Agitation of R1 was begun and the internal temperature adjusted to 10-20° C. A solution of 25% aqueous Na$_2$CO$_3$ (232 kg) was charged dropwise to the mixture until the pH was 8.0-9.0. The mixture was agitated for 20-60 min and then allowed to stand for 0.5-2 h. The layers were separated and the aqueous layer back extracted with i-PrOAc (200 kg). The combined organic layers were then concentrated to provide 69.5 kg of (R)-2-amino-2-(2-fluoro-5-nitrophenyl)-N-methylpropane-1-sulfonamide (x).

Step 6

(R)-5-(2-fluoro-5-nitrophenyl)-3-imino-2,5-dimethyl-1,2,4-thiadiazinane 1,1-dioxide

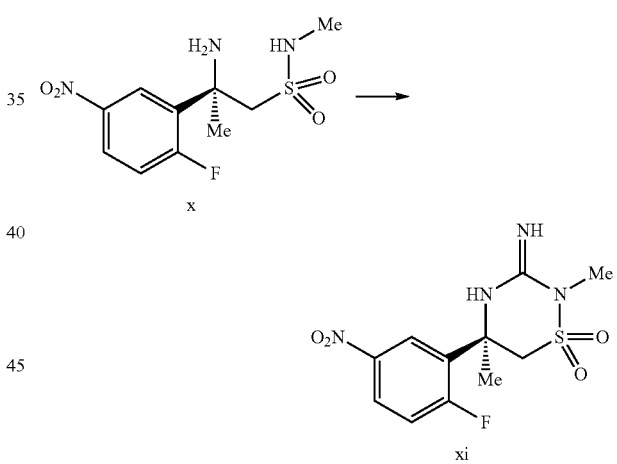

To a reactor (R1) equipped with a temperature probe, nitrogen inlet, and agitator was charged (R)-2-amino-2-(2-fluoro-5-nitrophenyl)-N-methylpropane-1-sulfonamide (x) (129.9 kg, 446.3 mol), MeCN (455 kg), and cyanogen bromide (75.2 kg, 710 mol). Agitation of R1 was begun and the internal temperature adjusted to 80-85° C. and maintained for 40-48 h. The mixture was then concentrated and flushed with MeCN until the concentration of cyanogen bromide was 210 ppm, at which point 0.1 M HCl (2788 kg) and i-PrOAc (1136 kg) were charged. The layers were separated and the organic layer washed twice with 0.1 M HCl (650 kg). The aqueous layer was back extracted with i-PrOAc (578 kg). The aqueous layer was basified with 40% NaOH (102 kg) until the pH was 6.5-7.5 and then seeded. To this mixture was charged 10% aqueous K$_2$CO$_3$ (460 kg) until the pH was 9-10. The resulting slurry was agitated for 4-6 h before the solids were collected to provide (R)-5-(2- fluoro-5-nitrophenyl)-3-imino-2,5-dimethyl-1,2,4-thiadiazinane 1,1-dioxide (xi) (113.5 kg).

Step 7

(R)-tert-butyl (5-(2-fluoro-5-nitrophenyl)-2,5-dimethyl-1,1-dioxido-1,2,4-thiadiazinan-3-ylidene)carbamate

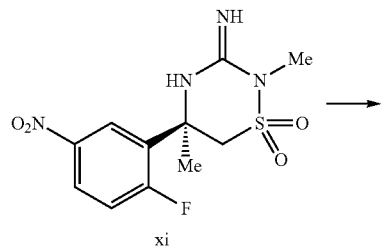

xi

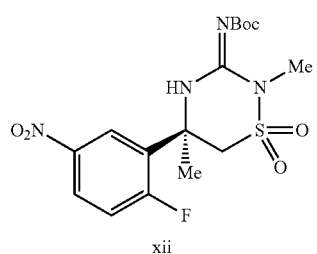

xii

To a reactor (R1) equipped with a temperature probe, nitrogen inlet, and agitator was charged (R)-5-(2-fluoro-5-nitrophenyl)-3-imino-2,5-dimethyl-1,2,4-thiadiazinane 1,1-dioxide (xi) (113.1 kg, 357.6 mol), CH₂Cl₂ (1518 kg), and Boc₂O (120.1 kg, 550.3 mol). The mixture in R1 was agitated for 16-24 h and then the solids removed. Heptane (50 kg) was charged to the filtrate followed by seed crystals. The resulting slurry was agitated for 2-4 h at 15-25° C. and then additional heptane (1656 kg) was charged. The solids were collected to provide (R)-tert-butyl (5-(2-fluoro-5-nitrophenyl)-2,5-dimethyl-1,1-dioxido-1,2,4-thiadiazinan-3-ylidene)carbamate (xii) (139.9 kg).

Step 8

(R)-tert-butyl (5-(5-amino-2-fluorophenyl)-2,5-dimethyl-1,1-dioxido-1,2,4-thiadiazinan-3-ylidene)carbamate

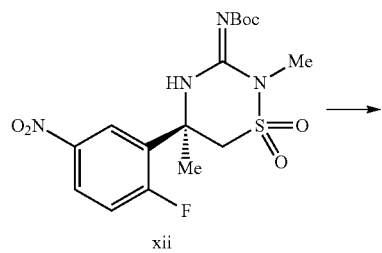

xii

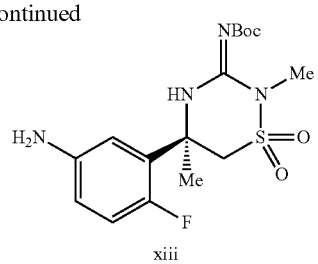

xiii

To a reactor (R1) equipped with a temperature probe, nitrogen inlet, and agitator was charged 5 weight % palladium on carbon (15 kg) and THF (200 L). Agitation of R1 was begun and the internal temperature adjusted to 0-5° C. A solution of (R)-tert-butyl (5-(2-fluoro-5-nitrophenyl)-2,5-dimethyl-1,1-dioxido-1,2,4-thiadiazinan-3-ylidene)carbamate (xii) (100 kg, 316.4 mol) in THF (350 L) was then charged. Hydrogen was introduced to a final pressure of 60 psi. When the reaction was judged complete, solids were removed and heptane (1500 L) was charged to the filtrate. The resulting solids were collected to provide (R)-tert-butyl (5-(5-amino-2-fluorophenyl)-2,5-dimethyl-1,1-dioxido-1,2, 4-thiadiazinan-3-ylidene)carbamate (xiii) (104.6 kg).

Step 9

Tosylate Salt of Verubecestat (xvi)

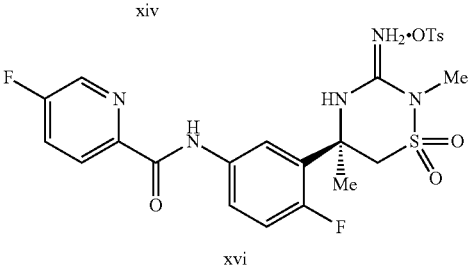

xvi

To a reactor (R1) equipped with a temperature probe, nitrogen inlet, and agitator was charged 2-MeTHF (1400 L). Agitation of R1 was begun and then (R)-tert-butyl (5-(5-amino-2-fluorophenyl)-2,5-dimethyl-1,1-dioxido-1,2,4-thiadiazinan-3-ylidene)carbamate (xiii) (138 kg) and 5-fluoropicolinic acid (xiv) (61 kg) were charged. Diisopropylethylamine (142 kg) was then charged to R1, followed by 1-propanephosphoric acid cyclic anhydride (50% solution in THF, 297 kg). The mixture was agitated at 20-25° C. until the reaction was judged complete, at which point the organics were washed twice with water (850 L). The organic layer was concentrated and the internal temperature of R1 adjusted to 50-55° C. To a second reactor (R2) was charged 2-MeTHF (262 L) and para-toluenesulfonic acid (164 kg), agitation was begun, and the mixture was warmed to 50-55° C. The contents of R1 were transferred to R2, maintaining the internal temperature. After aging, the tosylate salt of verubecestat (xvi) was generated.

Step 10

Verubecestat xvi verubecestat

To a reactor (R1) equipped with a temperature probe, nitrogen inlet, and agitator was charged EtOAc (1267 L) followed by the tosylate salt of verubecestat (xvi) (156 kg). Agitation of R1 was begun and the reaction mixture kept at 15-20° C. To R1 was charged 1 M aqueous $K_2CO_3$ (376 kg) and the mixture agitated before the layers were allowed to settle and the bottom aqueous layer was removed; this process was repeated. Water (462 L) was then charged to R1 and the mixture agitated before the layers were allowed to settle and the bottom aqueous layer was removed, resulting in verubecestat in the organic layer. MS (m/z): [M+H] calc'd for $C_{12}H_{18}F_2N_5O_3S$, 410.1054, found, 410.1086.

Step 11: Optional Purification Step

The product of Step 10 may optionally be further purified as follows.

Verubecestat verubecestat verubecestat

To a reactor (R1) equipped with a temperature probe, nitrogen inlet, and agitator was charged EtOAc (120 L) followed by verubecestat (20 kg). Agitation of R1 was begun, the internal temperature adjusted to 45-50° C. and heptane (180 L) was charged. The internal temperature of R1 was adjusted to 20-25° C. The solids were collected and washed with heptane to provide (verubecestat) (19 kg).

STEP A describes the synthesis of N-(4-methoxybenzyl)-N-methylmethanesulfonamide (ii), which is used in STEP 3 above.

Step A:

Preparation of
N-(4-methoxybenzyl)-N-methylmethanesulfonamide i → ii

Compound (ii), used in Step 3 below, was prepared as follows. To a reactor (R1) equipped with a temperature probe, nitrogen inlet, and agitator was charged MeOH (92 kg) and 4-methoxybenzaldehyde (i) (230.0 kg, 1689 mol). Agitation of R1 was begun and the internal temperature adjusted to 0° C. A solution of methylamine (30% in EtOH, 209.8 kg, 2026 mol) was charged to R1 dropwise over 6 h. The internal temperature of R1 was then adjusted to 20° C. and the mixture agitated until the condensation was judged to be complete, at which point the internal temperature was adjusted to 0° C. A second reactor (R2) was charged with THF (206 kg) followed by $NaBH_4$ (51.2 kg, 1351 mol). Agitation was begun and the reaction mixture from R1 was transferred to R2 over 8 h. The mixture was agitated until the reduction was judged to be complete. A third reactor (R3) was charged with water (115 kg) and 35% aqueous HCl (404 kg). Agitation of R3 was begun and the internal temperature was adjusted to 0° C. The reaction mixture from R2 was transferred to R3 over 12 h. The mixture was agitated until the reduction was judged to be complete. $CH_2Cl_2$ (969 kg) was charged to R3 followed by 50% aqueous NaOH (366 kg) over 6 h, at which point the internal temperature was adjusted to 20° C. The resulting solids were separated and washed with $CH_2Cl_2$ (157 kg) and the filtrate was transferred to R3. The layers were allowed to separate and the organic layer concentrated to approximately 1-2 volumes. $CH_2Cl_2$ (1220 kg) was charged to R3 and the contents concentrated; this process was repeated until the amount of residual water was judged to be satisfactory. Triethylamine (243 kg, 2400 mol) was charged to R3 and the contents of R3 transferred to a fourth reactor (R4). To R3 was charged methanesulfonyl chloride (223 kg, 1947 mol) and $CH_2Cl_2$ (635 kg), agitation was begun, and the internal temperature was adjusted to 0° C. The mixture in R4 was transferred to R3 dropwise over 12 h and then R3 was further agitated for 6 h. Water (572 kg) was then charged to R3 and the internal temperature adjusted to 20° C. The layers were allowed to separate and the organic layer washed twice with 2% aqueous NaCl (564 kg). The organic layer was concentrated under reduced pressure below 25° C. and then heptane (30 kg) was charged dropwise, followed by seed crystals (8 g) and additional heptane (1517 kg) over 20 h. The resulting slurry was agitated for 8 h before the solids were collected and washed with 10% $CH_2Cl_2$ in heptane (320 kg) to provide N-(4-methoxybenzyl)-N-methylmethanesulfonamide (ii) (290.8 kg).

Crystalline Forms of Verubecestat

In its many embodiments, the present invention provides four novel crystalline forms of verubecestat, including two novel crystalline forms of verubecestat and two novel forms of the tosylate salt of verubecestat (which may be referred to herein, individually or collectively, as "Crystalline Forms according to the invention"), specifically: Crystalline Tosylate Form 2 of Verubecestat, Crystalline Tosylate Hydrate Form 1 of Verubecestat, Crystalline Hemihydrate Form 1 of Verubecestat, and Crystalline Monohydrate Form 1 of Verubecestat.

X-ray powder diffraction (XRPD) studies, differential scanning calorimeter (DSC) studies, and/or thermogravimetric analysis (TGA) are widely used to characterize molecular structures, crystallinity, and polymorphism and were used where indicated to characterize the crystalline forms of verubecestat disclosed herein.

X-ray powder diffraction data reported herein were acquired using a Panalytical X-pert Pro PW3040 System™ or a Rigaku Model: D/Max-2200/PC diffractometer with a scintillation counter detector. The Panalytical X-pert Pro PW3040 System™ was configured in the Bragg-Brentano configuration and equipped with a Cu radiation source with monochromatization to Kα achieved using a Nickel filter ("Cu K alpha radiation"). Data were acquired between 2 and 40° 2 theta. Samples were prepared on a shallow cavity zero background silicon holder. For the data collected using the Rigaku Model: D/Max-2200/PC diffractometer with a scintillation counter detector, samples were prepared by lightly packing the material onto a silicon zero background holder followed by gentle smoothing to produce a flat sample surface. Copper (Kα) radiation generated at 44.0 kV and 40.0 mA was used. The sample was analyzed from 2 to 40 degrees 2 Theta with a step size of 0.02 degrees over step durations of 0.6 seconds. Those skilled in the art will recognize that the measurements of the PXRD peak locations for a given crystalline form of the same compound will vary within a margin of error. Variability can depend on such factors as the system, methodology, sample, and conditions used for measurement. As will also be appreciated by the skilled crystallographer, the intensities of the various peaks reported in the Figures below may vary due to a number of factors such as orientation effects of crystals in the X-ray beam, the purity of the material being analyzed, and/or the degree of crystallinity of the sample. The skilled crystallographer also will appreciate that measurements using a different wavelength will result in different shifts according to the Bragg-Brentano equation. Such further PXRD patterns generated by use of alternative wavelengths are considered to be alternative representations of the PXRD patterns of the crystalline materials of the present invention and as such are within the scope of the present invention.

A differential scanning calorimeter (DSC) was used to monitor thermal events as a function of temperature increase. The DSC data reported herein were acquired using a TA Instruments 2920 Differential Scanning Calorimeter™ (model 2920) or a TA Instruments Differential Scanning Calorimeter™, model Q1000 (New Castle, Del.) (model Q1000). The data acquired using the model 2920 was gathered on samples in aluminum pans which were heated from 25 to 250° C. at a heating rate of 10° C./min. For the data acquired using model Q1000, approximately 1 to 5 milligrams of sample were sealed in hermetic aluminum pans and two pinholes were punched into the lid of each sample pan. Analyses were conducted under a nitrogen purge of 50 mL per minute with a heating rate of 10° C. per minute. Instruments were calibrated with high purity indium. Those skilled in the art will appreciate that the accuracy of measurements will vary within a margin of error. The accuracy of the measured sample temperature with this method is within about +/−1° C., and the heat of fusion can be measured within a relative error of about +/−5%. The heat flow, which was normalized by a sample weight, was plotted versus the measured sample temperature. The data were reported in units of watts/gram ("W/g"). The plot was made with the endothermic peaks pointing down.

Thermogravimetric analysis data reported herein was acquired using a TA Q 500 Thermogravimetric Analyzer or a TA Instruments, model Q500 (New Castle, Del.), optionally with a Nicolet iS10 FTIR interface ThermoFisher Scientific (West Caldwell, N.J.). Approximately 5 to 15 milligrams of the compound was placed in a platinum pan and heated at 10° C. per minute from room temperature to 350° C. under a nitrogen purge with a flow rate of 55 mL/min.

Crystalline Tosylate Form 2 of Verubecestat

In one embodiment, the present invention provides a novel crystalline form of the tosylate salt of Verubecestat: hereinafter "Crystalline Tosylate Form 2" (or "Tosylate Form 2") of Verubecestat. Crystalline Tosylate Form 2 of Verubecestat was prepared according to the following procedure. The use of seed crystal in the preparation described below is regarded as an optional step.

Preparation of Crystalline Tosylate Form 2 of Verubecestat

Crystalline Tosylate Form 2 of Verubecestat was obtained from Crystalline Tosylate Form 1 of Verubecestat as follows. After aging the tosylate salt of verubecestat obtained in Step 9 above, the internal temperature of R2 (second reactor) was adjusted to 15-20° C. and the solids collected to provide the tosylate salt of verubecestat (154 kg). The resulting form of the tosylate salt of verubecestat obtained by this step was verified to be Tosylate Form 1 of the tosylate salt of verubecestat, which exhibited the following PXRD peak locations.

TABLE 1A

| 2 theta (degrees) | d-spacing (angstroms) |
| --- | --- |
| 6.84 | 12.91 |
| 9.042 | 9.77 |
| 11.84 | 7.45 |
| 12.40 | 7.14 |
| 13.60 | 6.51 |
| 14.26 | 6.21 |
| 14.66 | 6.03 |
| 15.78 | 5.62 |

TABLE 1A-continued

| 2 theta (degrees) | d-spacing (angstroms) |
|---|---|
| 17.60 | 5.04 |
| 18.04 | 4.91 |
| 19.14 | 4.63 |
| 19.76 | 4.49 |
| 20.38 | 4.36 |
| 21.34 | 4.16 |
| 22.28 | 3.99 |
| 23.16 | 3.84 |
| 23.70 | 3.75 |
| 24.28 | 3.66 |
| 24.58 | 3.62 |
| 26.04 | 3.42 |
| 27.24 | 3.27 |
| 27.94 | 3.19 |
| 28.82 | 3.09 |
| 29.16 | 3.06 |
| 29.84 | 2.99 |
| 30.30 | 2.95 |
| 31.00 | 2.88 |
| 31.84 | 2.81 |
| 32.80 | 2.73 |
| 33.50 | 2.67 |
| 34.34 | 2.61 |
| 35.54 | 2.52 |
| 36.24 | 2.48 |
| 37.14 | 2.42 |
| 38.28 | 2.35 |
| 38.94 | 2.31 |

104.7 milligrams of the Crystalline Tosylate Form 1 of Verubecestat was weighed into a 4 milliliter amber glass vial. 1.0 milliliter of dichloromethane was added. A suspension formed. A Teflon stir bar was added and the vial was sealed with a teflon lined cap. The suspension was stirred at room temperature for a total of 10 days. The vial was centrifuged to collect the solids. The solvent was removed using a glass pasture pipette. The wet cake sample was dried under dynamic house vacuum at room temperature for 24 hours to obtain Crystalline Tosylate Form 2 of Verubecestat.

Physical Characterization of Crystalline Tosylate Form 2 of Verubecestat

Powder X-Ray Diffraction

Using the Panalytical X-pert Pro PW3040 System™ and methods described above, the Crystalline Tosylate Form 2 of Verubecestat was subjected to PXRD analysis. A PXRD pattern was generated and is displayed in FIG. 1. The intensity of the peaks (y-axis is in counts per second) is plotted versus the 2Θ angle (x-axis is in degrees 2Θ). In addition, the data were plotted with detector counts normalized for the collection time per step versus the 2Θ angle. Peak locations (on the 2Θ x-axis) consistent with these profiles are displayed in Table 1B. The locations of these PXRD peaks are characteristic of the Crystalline Tosylate Form 2 of Verubecestat.

TABLE 1B

| 2Θ (degrees) | d-spacing (angstroms) |
|---|---|
| 5.38 | 16.41 |
| 8.14 | 10.85 |
| 10.80 | 8.18 |
| 11.68 | 7.57 |
| 14.40 | 6.15 |
| 14.82 | 6.00 |
| 15.54 | 5.70 |
| 16.34 | 5.42 |
| 17.68 | 5.01 |

TABLE 1B-continued

| 2Θ (degrees) | d-spacing (angstroms) |
|---|---|
| 19.48 | 4.55 |
| 20.28 | 4.38 |
| 21.08 | 4.21 |
| 21.50 | 4.13 |
| 23.56 | 3.77 |
| 24.38 | 3.65 |
| 25.26 | 3.52 |
| 25.56 | 3.48 |
| 26.04 | 3.42 |
| 26.98 | 3.30 |
| 27.96 | 3.19 |
| 29.12 | 3.06 |
| 30.12 | 2.96 |
| 32.04 | 2.79 |
| 33.00 | 2.71 |
| 33.42 | 2.68 |
| 34.38 | 2.61 |
| 35.72 | 2.51 |
| 36.72 | 2.45 |
| 37.30 | 2.41 |
| 38.20 | 2.35 |
| 38.56 | 2.33 |
| 39.30 | 2.29 |

Starting with the PXRD peak locations of the Crystalline Tosylate Form 2 of Verubecestat as displayed in Table 1B, the most characteristic peak locations can be selected and grouped by relative intensity to distinguish this crystalline structure from others. This selection of unique peaks is displayed in Table 1C. Thus, in one embodiment, the crystalline structure of the inventive Crystalline Tosylate Form 2 of Verubecestat may be identified by the Peak Location Group 1, consisting of four characteristic PXRD peak locations. In another embodiment, the crystalline structure of the inventive Crystalline Tosylate Form 2 of Verubecestat may be identified by the Peak Location Group No. 2, consisting of the four characteristic PXRD peak locations of Group No. 1 and an additional four peak locations. In another embodiment, the crystalline structure of the inventive Crystalline Tosylate Form 2 of Verubecestat may be identified by the Peak Location Group No. 3, consisting of the eight characteristic PXRD peak locations of Group No. 2 and an additional four peak locations.

TABLE 1C

| Peak Location Group No | Peak Locations (Degrees 2 Theta) | Peak Locations (Angstroms) |
|---|---|---|
| 1 | 5.38 | 16.41 |
|  | 8.14 | 10.85 |
|  | 16.34 | 5.421 |
|  | 11.68 | 7.570 |
| 2 | 5.38 | 16.41 |
|  | 8.14 | 10.85 |
|  | 16.34 | 5.421 |
|  | 11.68 | 7.570 |
|  | 14.82 | 5.973 |
|  | 19.48 | 4.553 |
|  | 24.38 | 3.648 |
|  | 14.40 | 6.146 |
| 3 | 5.38 | 16.41 |
|  | 8.14 | 10.85 |
|  | 16.34 | 5.421 |
|  | 11.68 | 7.570 |
|  | 14.82 | 5.973 |
|  | 19.48 | 4.553 |
|  | 24.38 | 3.648 |
|  | 14.40 | 6.146 |
|  | 23.56 | 3.773 |

TABLE 1C-continued

| Peak Location Group No | Peak Locations (Degrees 2 Theta) | Peak Locations (Angstroms) |
|---|---|---|
| | 21.08 | 4.211 |
| | 26.98 | 3.302 |
| | 30.12 | 2.965 |

Differential Scanning Calorimetry

Figure 2:
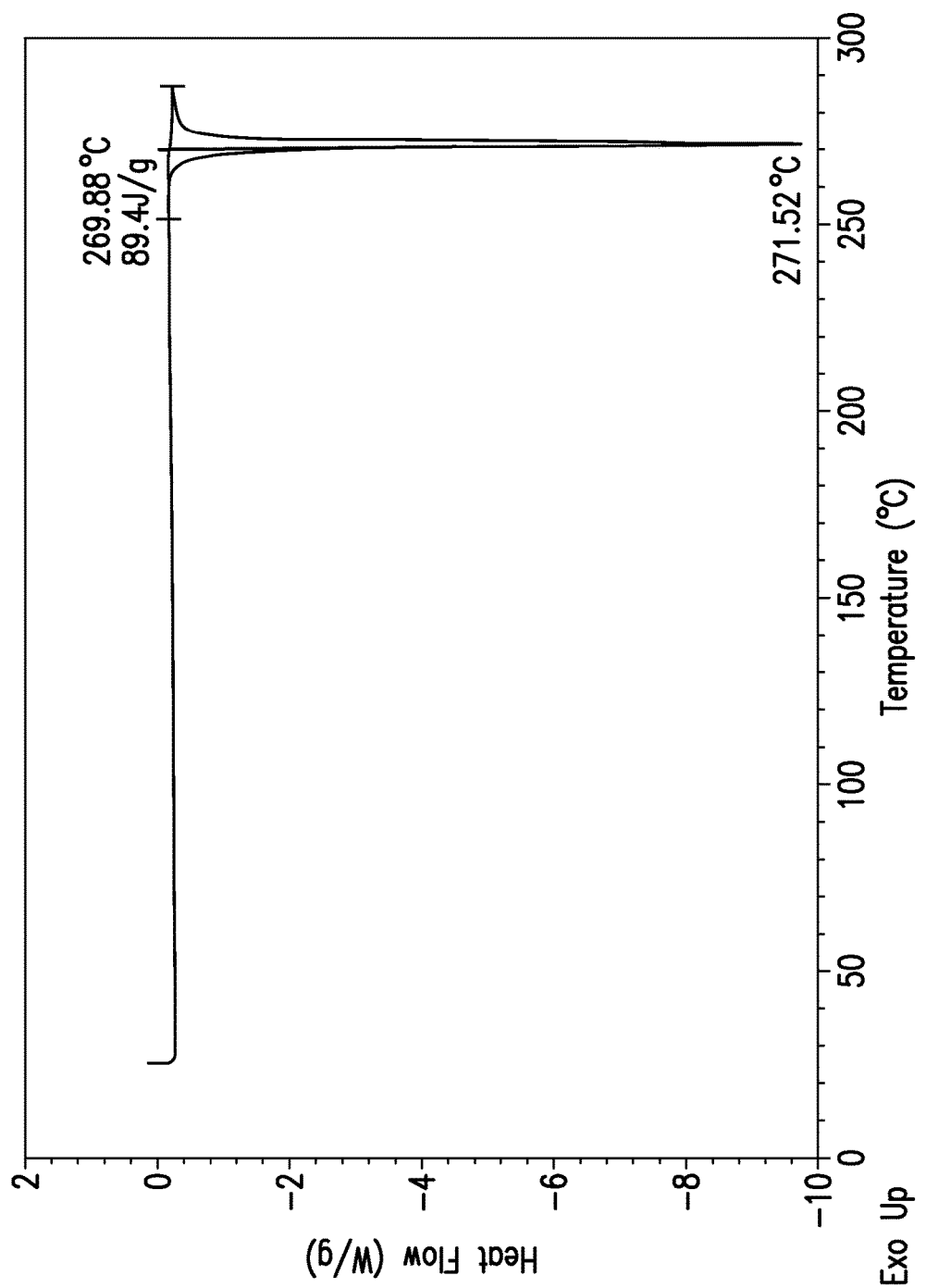
FIG. 2 is a graph of a differential scanning calorimetry ("DSC") thermogram of Crystalline Tosylate Form 2 of Verubecestat. The graph plots the normalized heat flow in units of Watts/gram (W/g) versus the measured sample temperature (° C.) with exotherms up.

Using the differential scanning calorimetry (DSC) equipment and procedures described above, the Crystalline Tosylate Form 2 of Verubecestat was subjected to DSC analysis. FIG. 2 depicts a DSC profile obtained for the Crystalline Tosylate Form 2 of Verubecestat. FIG. 2 shows a single sharp melting endotherm with an extrapolated onset temperature of 269.88° C. and a peak temperature of 271.52° C., which is indicative of a single crystalline species. The heat of fusion was 89.4 Joules/gram (J/g). The combination of melt temperature and heat of fusion can be used to distinguish Crystalline Tosylate Form 2 of Verubecestat from other crystal forms of Verubecestat.

Thermogravimetric Analysis

Figure 3:
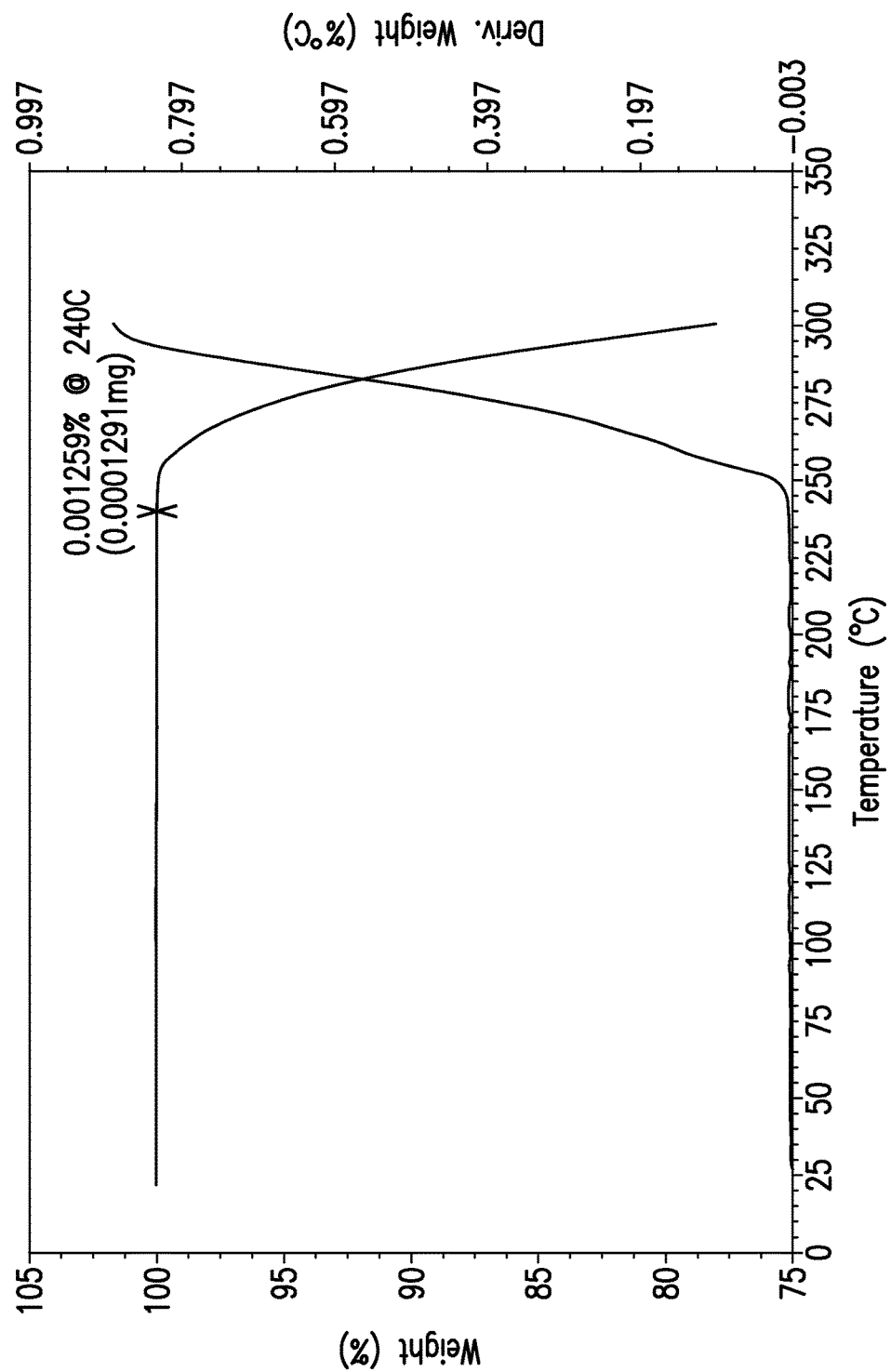
FIG. 3 is a graph of a thermal gravimetric analysis ("TGA") of Crystalline Tosylate Form 2 of Verubecestat. The graph plots the weight (percentage) against temperature (° C.).

Using the thermogravimetric analysis (TGA) equipment and procedures described above, the Crystalline Tosylate Form 2 of Verubecestat was subjected to TGA analysis. FIG. 3 shows TGA data for Crystalline Tosylate Form 2 of Verubecestat. The data do not show any significant thermal decomposition or weight loss attributable to the presence of solvent or other volatiles occurring below the melting point of the crystal.

Crystalline Tosylate Hydrate Form 1 of Verubecestat

In another embodiment, the present invention provides a novel crystalline form of the Verubecestat referred to herein as "Crystalline Tosylate Hydrate Form 1" (or "Tosylate Hydrate Form 1") of Verubecestat. Crystalline Tosylate Hydrate Form 1 of Verubecestat was prepared according to the following procedure. The use of seed crystal in the preparation described below is regarded as an optional step.

Preparation of Crystalline Tosylate Hydrate Form 1 of Verubecestat 95.6 milligrams of Crystalline Tosylate Form 1 of Verubecestat obtained as described above was weighed into a 4 milliliter amber glass vial. 0.25 milliliter of water and 0.75 milliliters of methanol was added. A suspension formed. A Teflon stir bar was added and the vial was sealed with a teflon lined cap. The suspension was stirred at 4° C. for a total of 10 days. The vial was centrifuged to collect the solids. The solvent was removed using a glass pasture pipette. The wet cake sample was dried under dynamic house vacuum at room temperature for 24 hours to obtain Crystalline Tosylate Hydrate Form 1 of Verubecestat.

Figure 4:
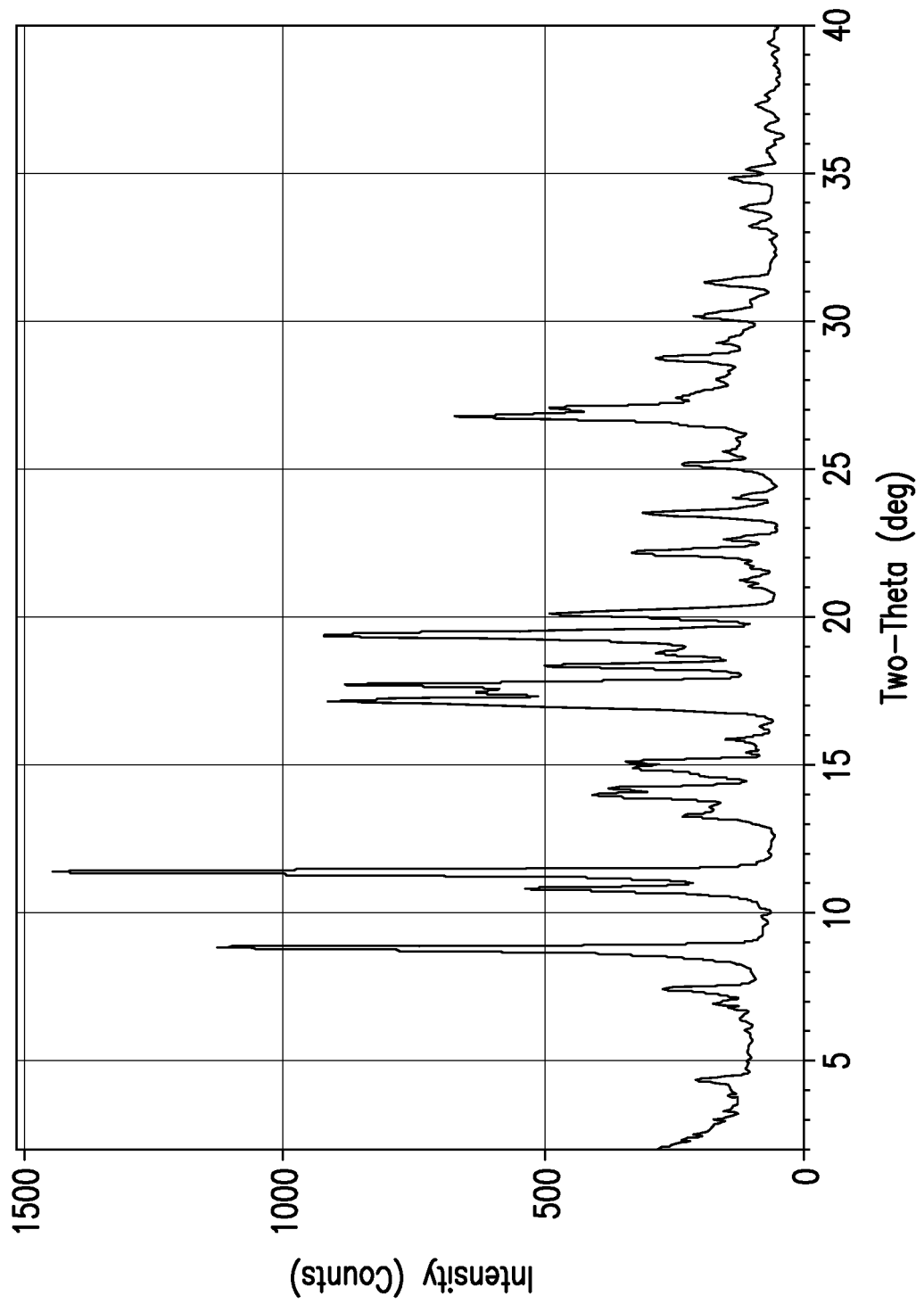
FIG. 4 is a graph of a Powder X-Ray Diffraction ("PXRD") pattern of Crystalline Tosylate Hydrate Form 1 of Verubecestat, generated using the equipment and methods described herein. The graph plots the intensity of the peaks as defined by counts per second versus the diffraction angle 2Θ (2 theta) in degrees.

Physical Characterization of Crystalline Tosylate Hydrate Form 1 of Verubecestat Powder X-Ray Diffraction Using the Panalytical X-pert Pro PW3040 System™ or a Rigaku Model: D/Max-2200/PC diffractometer with a scintillation counter detector and methods described above, the Crystalline Tosylate Hydrate Form 1 of Verubecestat was subjected to PXRD analysis. A PXRD pattern was generated and is displayed in FIG. 4. The intensity of the peaks (y-axis is in counts per second) is plotted versus the 2Θ angle (x-axis is in degrees 2Θ). In addition, the data were plotted with detector counts normalized for the collection time per step versus the 2Θ angle. Peak locations (on the 2Θ x-axis) consistent with these profiles are displayed in Table 2A. The locations of these PXRD peaks are characteristic of the Crystalline Tosylate Hydrate Form 1 of Verubecestat.

TABLE 2A

| 2Θ (degrees) | d-spacing (angstroms) |
|---|---|
| 4.34 | 20.34 |
| 6.36 | 13.89 |
| 6.94 | 12.73 |
| 7.44 | 11.87 |
| 8.78 | 10.06 |
| 10.76 | 8.21 |
| 11.32 | 7.81 |
| 13.26 | 6.67 |
| 14.00 | 6.32 |
| 14.26 | 6.21 |
| 15.08 | 5.87 |
| 16.22 | 5.46 |
| 17.14 | 5.17 |
| 17.72 | 5.00 |
| 18.38 | 4.82 |
| 19.32 | 4.59 |
| 20.02 | 4.43 |
| 21.28 | 4.17 |
| 22.02 | 4.03 |
| 22.66 | 3.92 |
| 23.46 | 3.79 |
| 23.70 | 3.75 |
| 24.02 | 3.70 |
| 25.18 | 3.53 |
| 25.52 | 3.49 |
| 26.00 | 3.42 |
| 26.76 | 3.33 |
| 27.04 | 3.29 |
| 28.24 | 3.16 |
| 28.86 | 3.09 |
| 29.32 | 3.04 |
| 29.74 | 3.00 |
| 30.46 | 2.93 |
| 31.30 | 2.86 |
| 32.62 | 2.74 |
| 33.70 | 2.66 |
| 34.76 | 2.58 |
| 35.12 | 2.55 |
| 35.70 | 2.51 |
| 35.98 | 2.50 |
| 36.66 | 2.45 |
| 37.14 | 2.42 |
| 37.40 | 2.403 |
| 38.60 | 2.33 |
| 39.02 | 2.31 |
| 39.40 | 2.29 |

Starting with the PXRD peak locations of the Crystalline Tosylate Hydrate Form 1 of Verubecestat as displayed in Table 2A, the most characteristic peak locations can be selected and grouped by relative intensity to distinguish this crystalline structure from others. This selection of unique peaks is displayed in Table 2B. Thus, in one embodiment, the crystalline structure of the inventive Crystalline Tosylate Hydrate Form 1 of Verubecestat may be identified by the Peak Location Group 1, consisting of four characteristic PXRD peak locations. In another embodiment, the crystalline structure of the inventive Crystalline Tosylate Hydrate Form 1 of Verubecestat may be identified by the Peak Location Group No. 2, consisting of the four characteristic PXRD peak locations of Group No. 1 and an additional four peak locations. In another embodiment, the crystalline structure of the inventive Crystalline Tosylate Hydrate Form 1 of Verubecestat may be identified by the Peak Location Group No. 3, consisting of the eight characteristic PXRD peak locations of Group No. 2 and an additional four peak locations.

TABLE 2B

| Peak Location Group No | Peak Locations (Degrees 2 Theta) | Peak Locations (Angstroms) |
|---|---|---|
| 1 | 4.34 | 20.34 |
|   | 8.78 | 10.06 |
|   | 17.14 | 5.17 |
|   | 7.44 | 11.87 |
| 2 | 4.34 | 20.34 |
|   | 8.78 | 10.06 |
|   | 17.14 | 5.17 |
|   | 7.44 | 11.87 |
|   | 11.32 | 7.81 |
|   | 19.32 | 4.59 |
|   | 18.38 | 4.82 |
|   | 10.76 | 8.22 |
| 3 | 4.34 | 20.34 |
|   | 8.78 | 10.06 |
|   | 17.14 | 5.17 |
|   | 7.44 | 11.87 |
|   | 11.32 | 7.81 |
|   | 19.32 | 4.59 |
|   | 18.38 | 4.82 |
|   | 10.76 | 8.22 |
|   | 17.72 | 5.00 |
|   | 14.00 | 6.32 |
|   | 15.08 | 5.87 |
|   | 13.26 | 6.67 |

Differential Scanning Calorimetry

Figure 5:
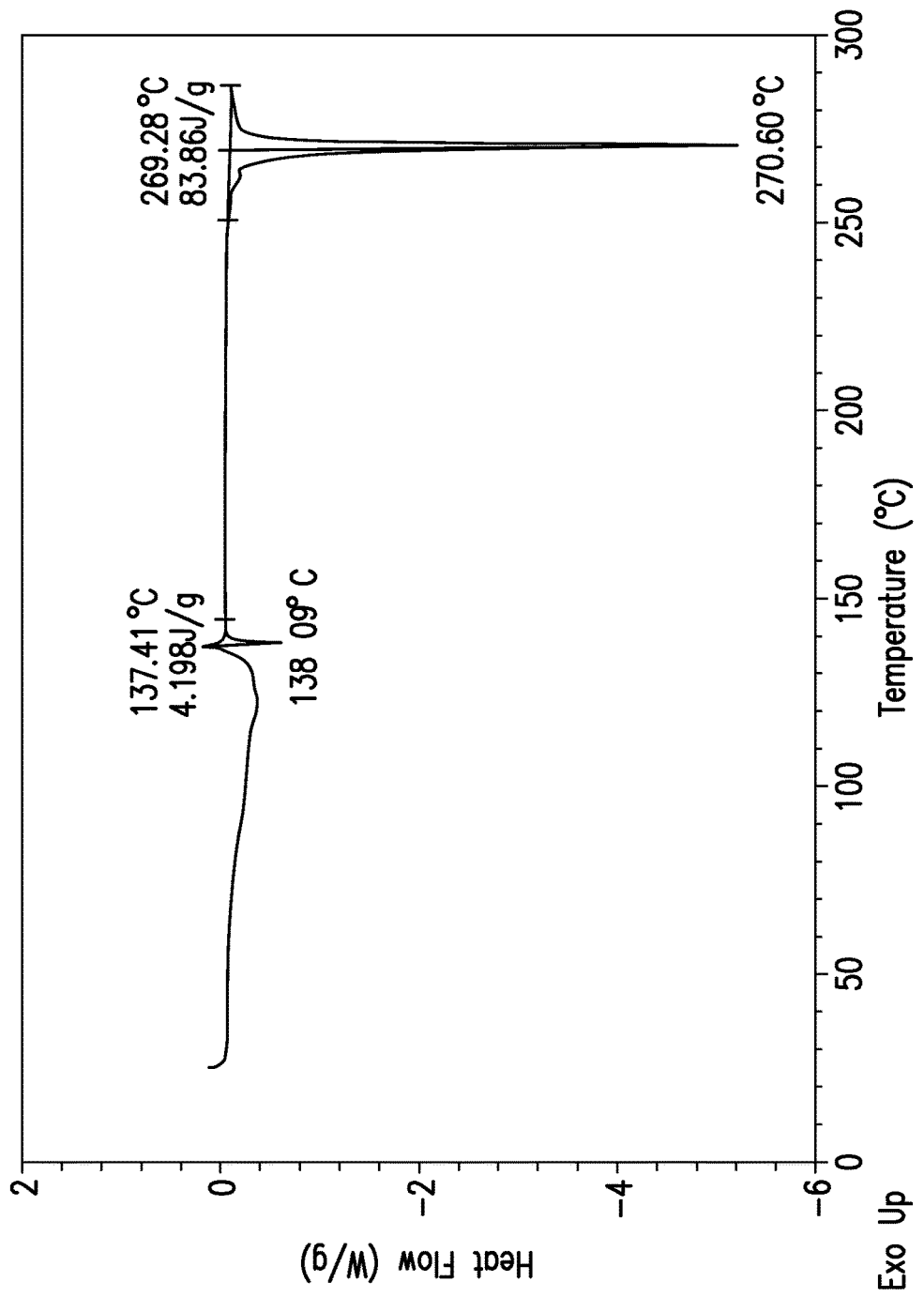
FIG. 5 is a graph of a differential scanning calorimetry ("DSC") thermogram of Crystalline Tosylate Hydrate Form 1 of Verubecestat. The graph plots the normalized heat flow in units of Watts/gram (W/g) versus the measured sample temperature (° C.) with exotherms up.

Using the differential scanning calorimetry (DSC) equipment and procedures described above, the Crystalline Tosylate Hydrate Form 1 of Verubecestat was subjected to DSC analysis. FIG. 5 depicts a DSC profile obtained for the Crystalline Tosylate Hydrate Form 1 of Verubecestat. FIG. 5 shows multiple events in the DSC data consistent with dehydration, conversion of the dehydrated hydrate into an anhydrous form, and melting of the anhydrous formed in the DSC analysis. The overall DSC profile can be used to distinguish Crystalline Tosylate Hydrate Form 1 of Verubecesant with other crystalline forms of Verubecesant.

Thermogravimetric Analysis

Figure 6:
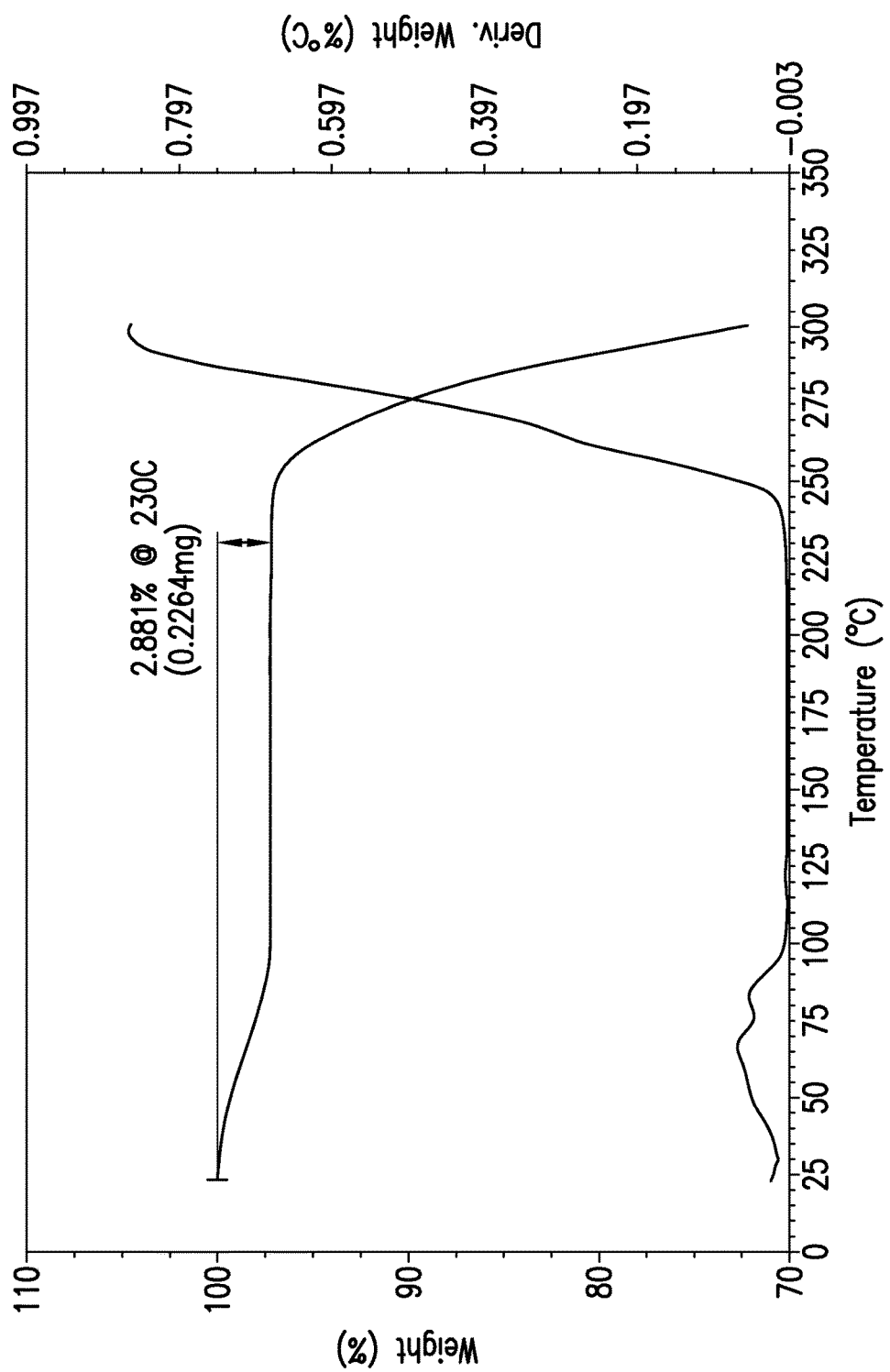
FIG. 6 is a graph of a thermal gravimetric analysis ("TGA") of Crystalline Tosylate Hydrate Form 1 of Verubecestat. The graph plots the weight (percentage) against temperature (° C.).

Using the thermogravimetric analysis (TGA) equipment and procedures described above, the Crystalline Tosylate Hydrate Form 1 of Verubecestat was subjected to TGA analysis. FIG. 6 shows TGA data for Crystalline Tosylate Hydrate Form 1 of Verubecestat. The data do not show any significant thermal decomposition or weight loss attributable to the presence of solvent or other volatiles occurring below the melting point of the crystal. The only weight loss observed as determined to be from water in hydrated crystal.

Crystalline Hemihydrate Form 1 of Verubecestat

In another embodiment, the present invention provides a novel crystalline form of the Verubecestat referred to herein as "Crystalline Hemihydrate Form 1" (or "Hemihydrate Form 1") of Verubecestat. Crystalline Hemihydrate Form 1 of Verubecestat was prepared according to the following procedure.

Preparation of Crystalline Hemihydrate Form 1 of Verubecestat

Crystalline Hemihydrate Form 1 of Verubecestat was obtained from Crystalline Anhydrous Form 1 of Verubecestat as follows. The organic layer comprising verubecestat obtained from Step 10 above was concentrated and warmed to 45-50° C., at which point heptane (144 L) was charged followed by seed crystals (3.2 kg). The resulting slurry was agitated and heptane (1022 L) was charged. The internal temperature of R1 was adjusted to 20-25° C. and the solids were collected and washed with heptane to provide Crystalline Anhydrous Form 1 of Verubecestat (101 kg). The resulting form of the free base of verubecestat obtained by this step was verified to be Anhydrous Form 1 of the Verubecestat, which exhibited the following PXRD peak locations.

TABLE 3A

| 2 theta (degrees) | d-spacing (angstroms) |
|---|---|
| 7.61 | 11.62 |
| 9.87 | 8.96 |
| 10.32 | 8.57 |
| 12.48 | 7.09 |
| 13.95 | 6.35 |
| 15.26 | 5.81 |
| 15.67 | 5.65 |
| 15.91 | 5.57 |
| 16.81 | 5.27 |
| 17.44 | 5.09 |
| 18.22 | 4.87 |
| 19.82 | 4.48 |
| 20.73 | 4.29 |
| 21.28 | 4.18 |
| 21.95 | 4.05 |
| 22.33 | 3.98 |
| 23.00 | 3.87 |
| 23.43 | 3.80 |
| 23.99 | 3.71 |
| 25.07 | 3.55 |
| 25.34 | 3.51 |
| 26.49 | 3.36 |
| 27.00 | 3.30 |
| 27.94 | 3.19 |
| 29.17 | 3.06 |
| 29.85 | 2.99 |
| 31.57 | 2.83 |
| 32.49 | 2.76 |
| 33.06 | 2.71 |
| 33.78 | 2.65 |
| 36.25 | 2.48 |
| 37.34 | 2.41 |
| 39.46 | 2.28 |

102.0 milligrams of Crystalline Anhydrous Form 1 of Verubecestat obtained as described above was weighed into a 4 milliliter clear glass vial. 1.0 milliliter of Acetone was added. A solution resulted. 2.0 milliliters of water was added in 1.0 milliliter increments. A suspension formed. A stir bar coated with PTFE was added and the vial was sealed with a PTFE lined cap. The suspension was stirred at room temperature for 24 hours. The vial was centrifuged to collect the solids. The solvent was removed using a glass pasture pipette. The wet cake sample was dried under dynamic house vacuum at room temperature for 24 hours, providing Crystalline Hemihydrate Form 1 of Verubecestat.

Physical Characterization of Crystalline Hemihydrate Form 1 of Verubecestat

Powder X-Ray Diffraction

Figure 7:
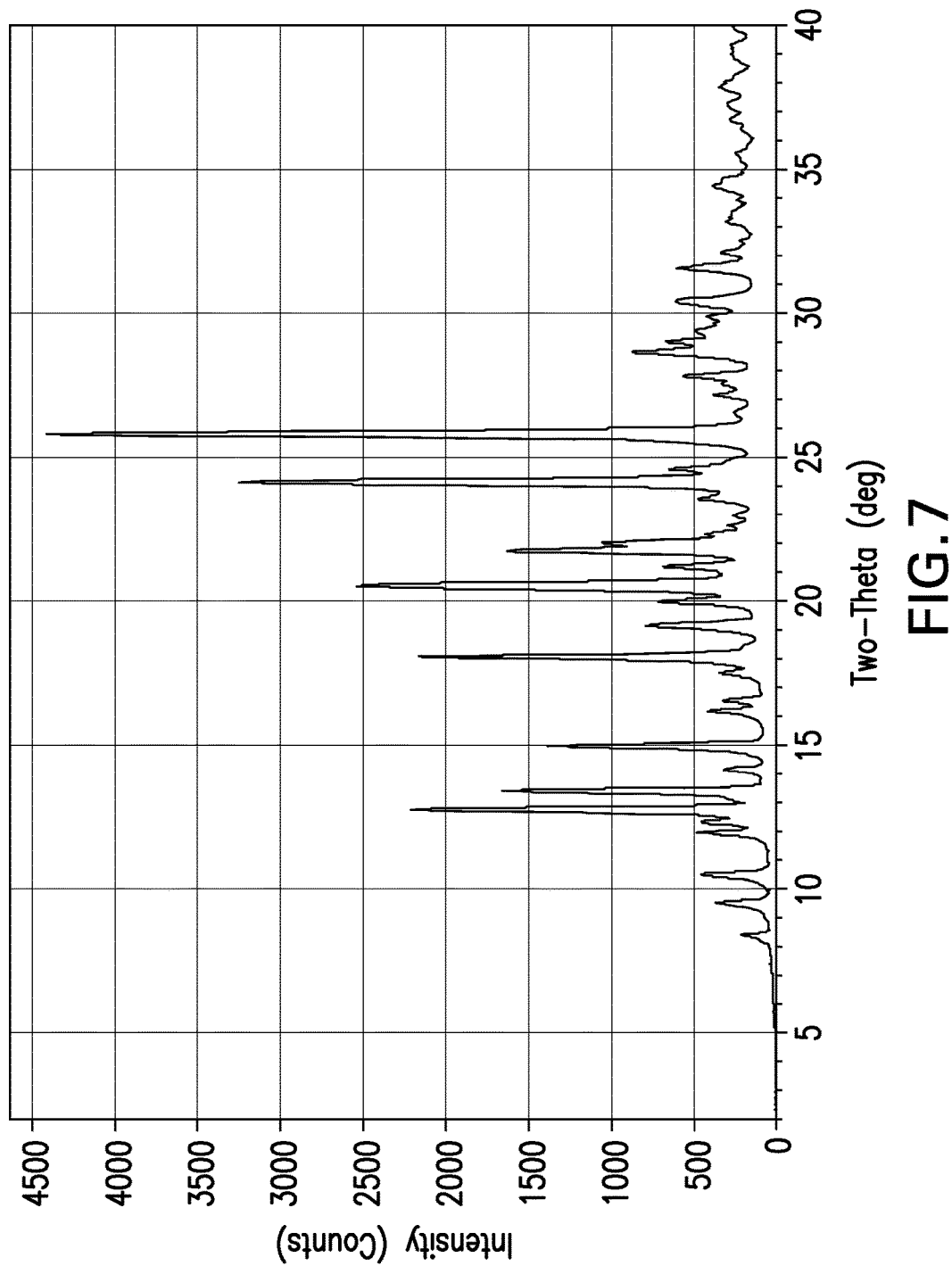
FIG. 7 is a graph of a Powder X-Ray Diffraction ("PXRD") pattern of Crystalline Hemihydrate Form 1 of Verubecestat, generated using the equipment and methods described herein. The graph plots the intensity of the peaks as defined by counts per second versus the diffraction angle 2Θ (2 theta) in degrees.

Using the Panalytical X-pert Pro PW3040 System™ or a Rigaku Model: D/Max-2200/PC diffractometer with a scintillation counter detector and methods described above, the Crystalline Hemihydrate Form 1 of Verubecestat obtained as described above was subjected to PXRD analysis. A PXRD pattern was generated and is displayed in FIG. 7. The intensity of the peaks (y-axis is in counts per second) is plotted versus the 2θ angle (x-axis is in degrees 2θ). In addition, the data were plotted with detector counts normalized for the collection time per step versus the 2θ angle. Peak locations (on the 2θ x-axis) consistent with these profiles are displayed in Table 3B. The locations of these PXRD peaks are characteristic of the Crystalline Hemihydrate Form 1 of Verubecestat.

TABLE 3B

| 2Θ (degrees) | d-spacing (angstroms) |
|---|---|
| 8.42 | 10.49 |
| 9.56 | 9.25 |
| 10.52 | 8.40 |
| 12.02 | 7.34 |
| 12.36 | 7.16 |
| 12.82 | 6.90 |
| 13.48 | 6.56 |
| 14.18 | 6.24 |
| 15.04 | 5.89 |
| 16.24 | 5.45 |
| 16.58 | 5.34 |
| 17.54 | 5.05 |
| 18.12 | 4.90 |
| 19.18 | 4.62 |
| 20.02 | 4.43 |
| 20.58 | 4.31 |
| 21.24 | 4.18 |
| 21.78 | 4.08 |
| 22.09 | 4.02 |
| 22.68 | 3.92 |
| 23.04 | 3.86 |
| 23.62 | 3.76 |
| 24.18 | 3.68 |
| 24.64 | 3.61 |
| 25.88 | 3.44 |
| 27.20 | 3.28 |
| 27.84 | 3.20 |
| 28.68 | 3.11 |
| 29.02 | 3.07 |
| 29.44 | 3.03 |
| 29.90 | 2.99 |
| 30.48 | 2.93 |
| 31.62 | 2.83 |
| 32.14 | 2.78 |
| 33.24 | 2.69 |
| 34.44 | 2.60 |
| 35.58 | 2.52 |
| 36.74 | 2.44 |
| 37.24 | 2.41 |
| 37.88 | 2.37 |
| 39.01 | 2.31 |
| 39.34 | 2.29 |

Starting with the PXRD peak locations of the Crystalline Hemihydrate Form 1 of Verubecestat as displayed in Table 3B, the most characteristic peak locations can be selected and grouped by relative intensity to distinguish this crystalline structure from others. This selection of unique peaks is displayed in Table 3C. Thus, in one embodiment, the crystalline structure of the inventive Crystalline Hemihydrate Form 1 of Verubecestat may be identified by the Peak Location Group 1, consisting of four characteristic PXRD peak locations. In another embodiment, the crystalline structure of the inventive Crystalline Hemihydrate Form 1 of Verubecestat may be identified by the Peak Location Group No. 2, consisting of the four characteristic PXRD peak locations of Group No. 1 and an additional four peak locations. In another embodiment, the crystalline structure of the inventive Crystalline Hemihydrate Form 1 of Verubecestat may be identified by the Peak Location Group No. 3, consisting of the eight characteristic PXRD peak locations of Group No. 2 and an additional four peak locations.

TABLE 3C

| Peak Location Group No | Peak Locations (Degrees 2 Theta) | Peak Locations (Angstroms) |
|---|---|---|
| 1 | 25.88 | 3.44 |
|   | 20.58 | 4.31 |
|   | 12.82 | 6.90 |
|   | 9.56 | 9.25 |
| 2 | 25.88 | 3.44 |
|   | 20.58 | 4.31 |
|   | 12.82 | 6.90 |
|   | 9.56 | 9.25 |
|   | 24.18 | 3.68 |
|   | 18.12 | 4.89 |
|   | 13.48 | 6.56 |
|   | 21.78 | 4.08 |
| 3 | 25.88 | 3.44 |
|   | 20.58 | 4.31 |
|   | 12.82 | 6.90 |
|   | 9.56 | 9.25 |
|   | 24.18 | 3.68 |
|   | 18.12 | 4.89 |
|   | 13.48 | 6.56 |
|   | 21.78 | 4.08 |
|   | 15.04 | 5.89 |
|   | 22.09 | 4.02 |
|   | 28.68 | 3.11 |
|   | 19.18 | 4.62 |

Differential Scanning Calorimetry

Figure 8:
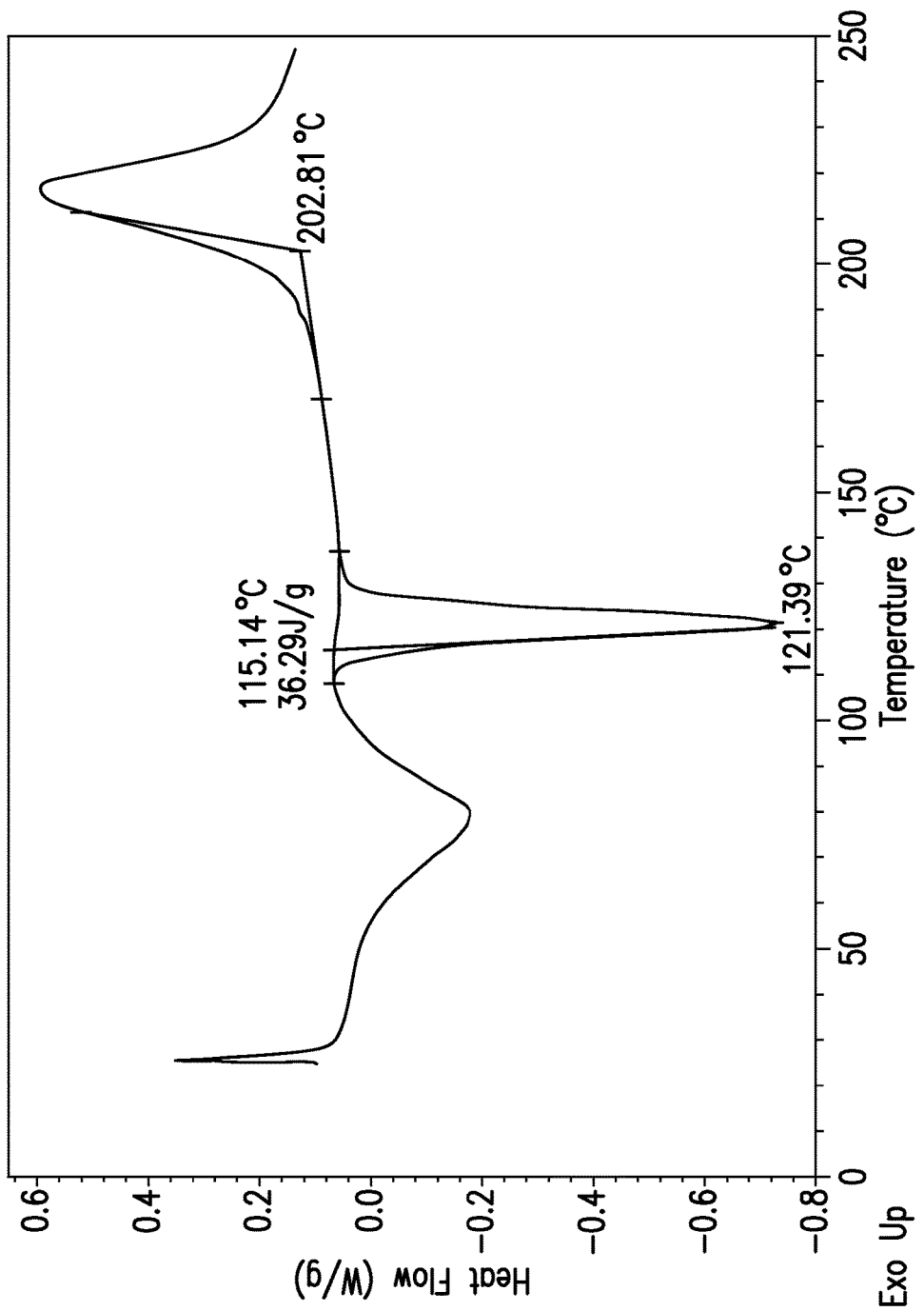
FIG. 8 is a graph of a differential scanning calorimetry ("DSC") thermogram of Crystalline Hemihydrate Form 1 of Verubecestat. The graph plots the normalized heat flow in units of Watts/gram (W/g) versus the measured sample temperature (° C.) with exotherms up.

Using the differential scanning calorimetry (DSC) equipment and procedures described above, the Crystalline Hemihydrate Form 1 of Verubecestat was subjected to DSC analysis. FIG. 8 depicts a DSC profile obtained for the Crystalline Hemihydrate Form 1 of Verubecestat. FIG. 8 shows multiple events in the DSC data consistent with dehydration and collapse of the dehydrated hydrate form. The overall DSC profile can be used to distinguish Crystalline Hemihydrate Form 1 of Verubecesant with other crystalline forms of Verubecesant.

Thermogravimetric Analysis

Figure 9:
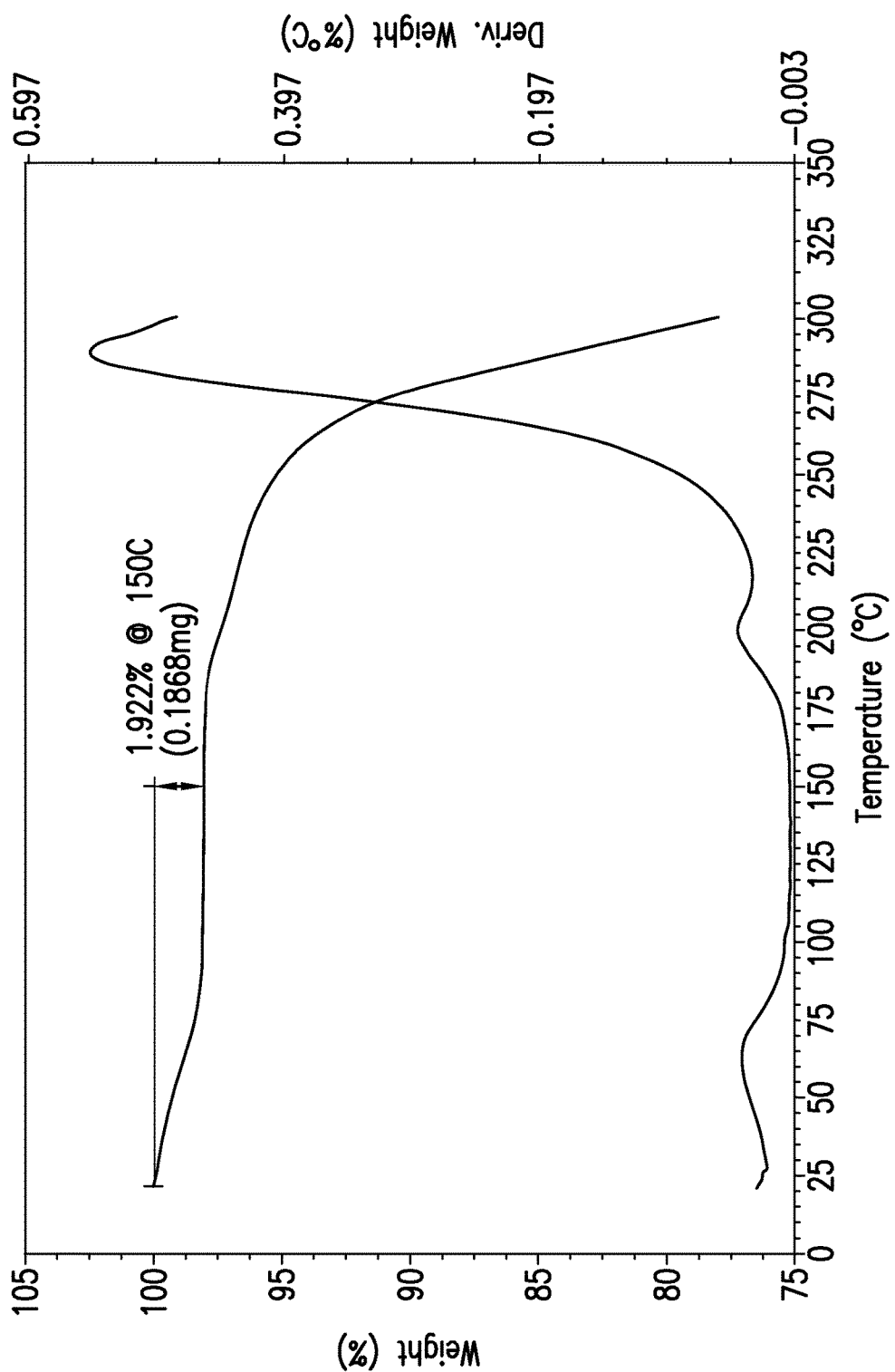
FIG. 9 is a graph of a thermal gravimetric analysis ("TGA") of Crystalline Hemihydrate Form 1 of Verubecestat. The graph plots the weight (percentage) against temperature (° C.).

Using the thermogravimetric analysis (TGA) equipment and procedures described above, the Crystalline Hemihydrate Form 1 of Verubecestat was subjected to TGA analysis. FIG. 9 shows TGA data for Crystalline Hemihydrate Form 1 of Verubecestat. The data do not show any significant thermal decomposition or weight loss attributable to the presence of solvent or other volatiles occurring below the melting point of the crystal. The only weight loss observed as determined to be from water in hydrated crystal.

Crystalline Monohydrate Form 1 of Verubecestat

In another embodiment, the present invention provides a novel crystalline form of the Verubecestat referred to herein as "Crystalline Monohydrate Form 1" (or "Monohydrate Form 1") of Verubecestat. Crystalline Monohydrate Form 1 of Verubecestat was prepared according to the following procedure.

Preparation of Crystalline Monohydrate Form 1 of Verubecestat 4.9 g Verubecestat, 32 mL isopropyl alcohol, and 8 mL water was added to EasyMax™ vessel and mixed. The batch was heated to 50° C. over 1 hour then cooled in solution to 20° C. 107 mg seed Crystalline Anhydrous Form 1 was added to the solution and seed bed was aged for 2 hr 10 min at 20 C. 60 mL water was added over 8 hr to reactor with stirring. The slurry sample was isolated, providing Crystalline Monohydrate Form 1 of Verubecestat.

Figure 10:
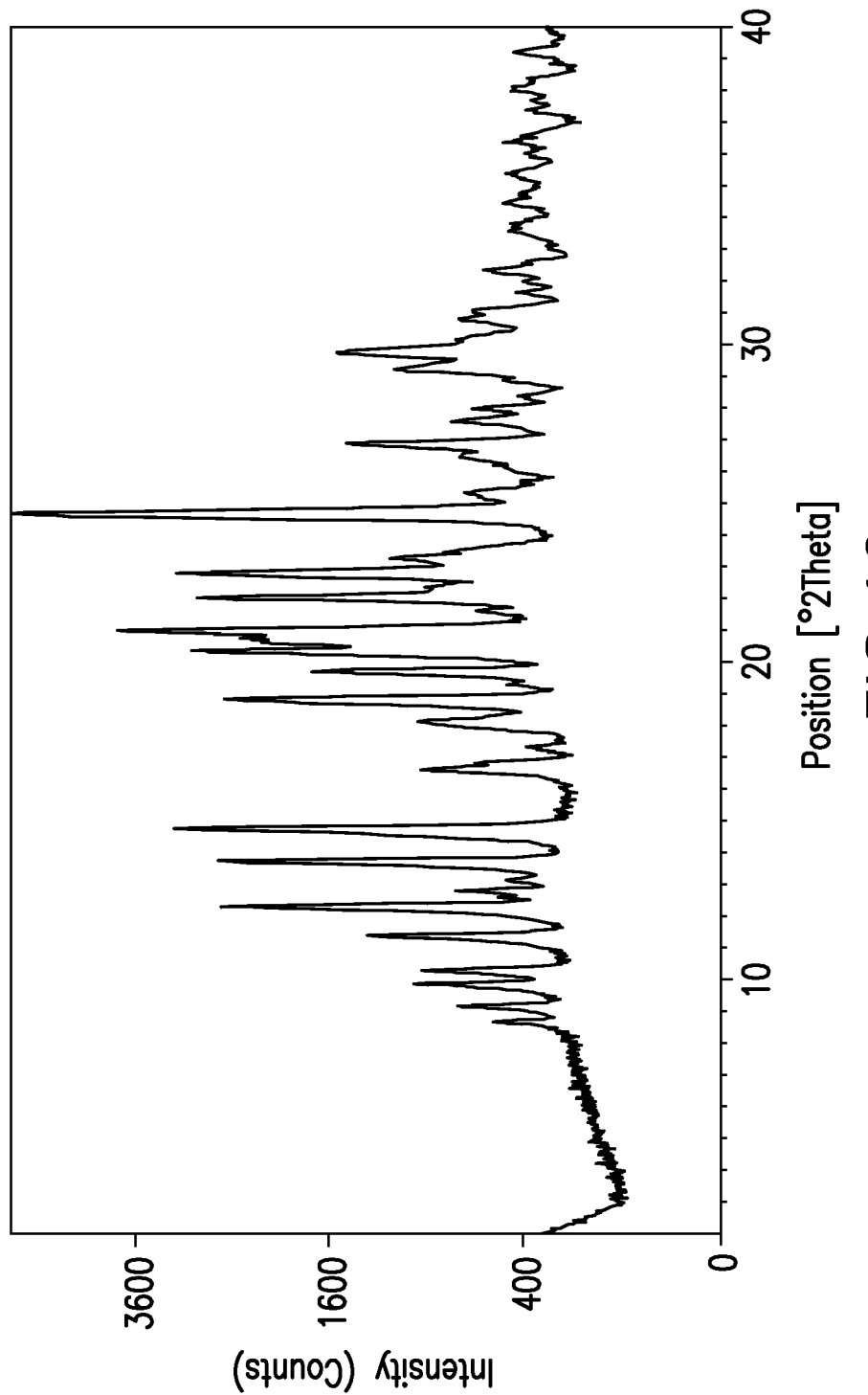
FIG. 10 is a graph of a Powder X-Ray Diffraction ("PXRD") pattern of Crystalline Monohydrate Form 1 of Verubecestat, generated using the equipment and methods described herein. The graph plots the intensity of the peaks as defined by counts per second versus the diffraction angle 2Θ (2 theta) in degrees.

Physical Characterization of Crystalline Monohydrate Form 1 of Verubecestat
Powder X-Ray Diffraction Using the Panalytical X-pert Pro PW3040 System™ or a Rigaku Model: D/Max-2200/PC diffractometer with a scintillation counter detector and methods described above, the Crystalline Monohydrate Form 1 of Verubecestat obtained as described above was subjected to PXRD analysis. A PXRD pattern was generated and is displayed in FIG. 10. The intensity of the peaks (y-axis is in counts per second) is plotted versus the 2Θ angle (x-axis is in degrees 2Θ). In addition, the data were plotted with detector counts normalized for the collection time per step versus the 2Θ angle. Peak locations (on the 2Θ x-axis) consistent with these profiles are displayed in Table 4A. The locations of these PXRD peaks are characteristic of the Crystalline Monohydrate Form 1 of Verubecestat.

TABLE 4A

| 2Θ (degrees) | d-spacing (angstroms) |
| --- | --- |
| 8.66 | 10.21 |
| 9.15 | 9.67 |
| 9.86 | 8.97 |
| 10.28 | 8.61 |
| 11.38 | 7.77 |
| 12.29 | 7.20 |
| 12.77 | 6.93 |
| 13.73 | 6.45 |
| 14.75 | 6.00 |
| 16.58 | 5.35 |
| 17.27 | 5.14 |
| 18.11 | 4.90 |
| 18.83 | 4.71 |
| 19.72 | 4.50 |
| 20.35 | 4.36 |
| 20.96 | 4.24 |
| 21.58 | 4.12 |
| 21.99 | 4.04 |
| 22.77 | 3.91 |
| 23.25 | 3.83 |
| 24.50 | 3.63 |
| 24.66 | 3.61 |
| 25.33 | 3.52 |
| 26.87 | 3.32 |
| 27.57 | 3.24 |
| 27.97 | 3.19 |
| 29.18 | 3.06 |
| 29.68 | 3.01 |
| 30.75 | 2.91 |
| 31.06 | 2.88 |
| 32.30 | 2.77 |
| 33.61 | 2.67 |
| 34.43 | 2.60 |
| 35.35 | 2.54 |
| 36.39 | 2.47 |
| 37.34 | 2.41 |
| 38.16 | 2.36 |
| 39.18 | 2.30 |

Starting with the PXRD peak locations of the Crystalline Monohydrate Form 1 of Verubecestat as displayed in Table 4A, the most characteristic peak locations can be selected and grouped by relative intensity to distinguish this crystalline structure from others. This selection of unique peaks is displayed in Table 4B. Thus, in one embodiment, the crystalline structure of the inventive Crystalline Monohydrate Form 1 of Verubecestat may be identified by the Peak Location Group 1, consisting of four characteristic PXRD peak locations. In another embodiment, the crystalline structure of the inventive Crystalline Monohydrate Form 1 of Verubecestat may be identified by the Peak Location Group No. 2, consisting of the four characteristic PXRD peak locations of Group No. 1 and an additional four peak locations. In another embodiment, the crystalline structure of the inventive Crystalline Monohydrate Form 1 of Verubecestat may be identified by the Peak Location Group No. 3, consisting of the eight characteristic PXRD peak locations of Group No. 2 and an additional four peak locations.

TABLE 4B

| Peak Location Group No. | Peak Location (degrees 2Θ) | d-spacing (angstroms) |
| --- | --- | --- |
| Group 1 | 8.66 | 10.21 |
| | 9.15 | 9.67 |
| | 11.38 | 7.77 |
| | 12.29 | 7.20 |
| Group 2 | 8.66 | 10.21 |
| | 9.15 | 9.67 |
| | 11.38 | 7.77 |
| | 12.29 | 7.20 |
| | 13.73 | 6.45 |
| | 14.75 | 6.00 |
| | 18.83 | 4.71 |
| | 19.72 | 4.50 |
| Group 3 | 8.66 | 10.21 |
| | 9.15 | 9.67 |
| | 11.38 | 7.77 |
| | 12.29 | 7.20 |
| | 13.73 | 6.45 |
| | 14.75 | 6.00 |
| | 18.83 | 4.71 |
| | 19.72 | 4.50 |
| | 20.35 | 4.36 |
| | 20.96 | 4.24 |
| | 22.77 | 3.91 |
| | 24.66 | 3.61 |

Differential Scanning Calorimetry

Figure 11:
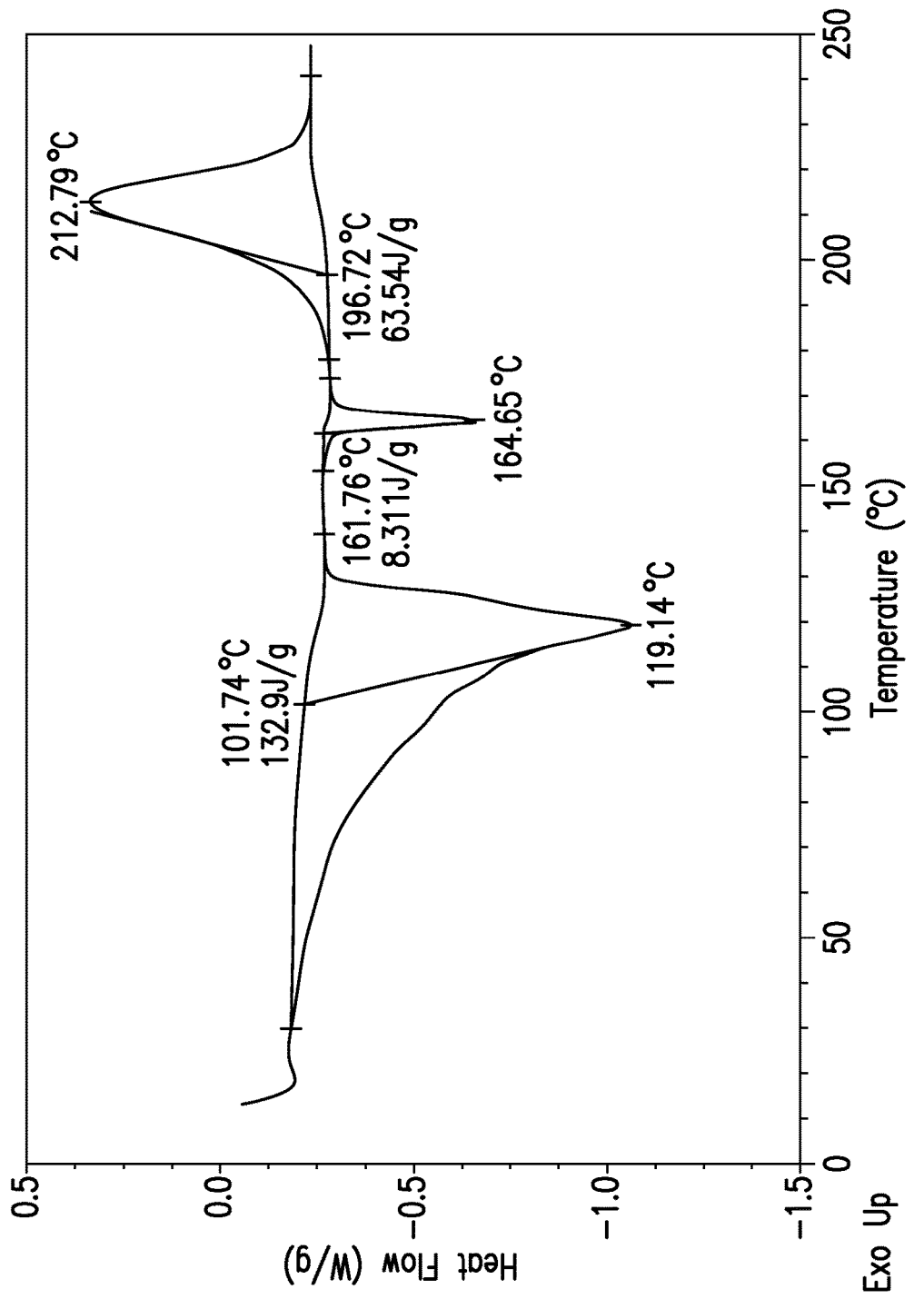
FIG. 11 is a graph of a differential scanning calorimetry ("DSC") thermogram of Crystalline Monohydrate Form 1 of Verubecestat. The graph plots the normalized heat flow in units of Watts/gram (W/g) versus the measured sample temperature (° C.) with exotherms up.

Using the differential scanning calorimetry (DSC) equipment and procedures described above, the Crystalline Monohydrate Form 1 of Verubecestat was subjected to DSC analysis. FIG. 11 depicts a DSC profile obtained for the Crystalline Monohydrate Form 1 of Verubecestat. The overall DSC profile can be used to distinguish Crystalline Monohydrate Form 1 of Verubecesant with other crystalline forms of Verubecesant.

Thermogravimetric Analysis

Figure 12:
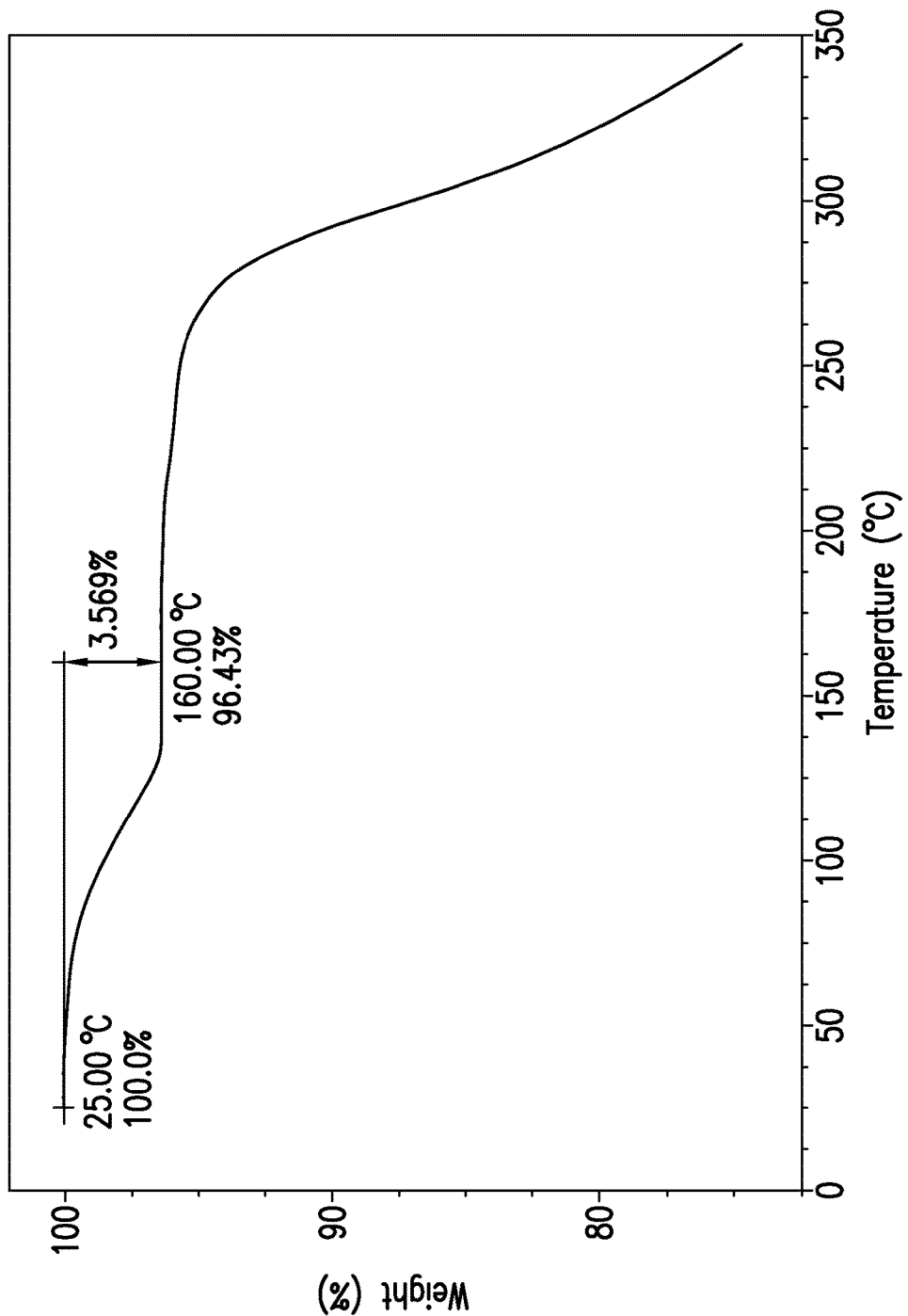
FIG. 12 is a graph of a thermal gravimetric analysis ("TGA") of Crystalline Monohydrate Form 1 of Verubecestat. The graph plots the weight (percentage) against temperature (° C.).

Using the thermogravimetric analysis (TGA) equipment and procedures described above, the Crystalline Monohydrate Form 1 of Verubecestat was subjected to TGA analysis. FIG. 12 shows TGA data for Crystalline Monohydrate Form 1 of Verubecestat. The data do not show any significant thermal decomposition or weight loss attributable to the presence of solvent or other volatiles occurring below the melting point of the crystal. The only weight loss observed as determined to be from water in hydrated crystal.

Properties

The crystalline forms according to the invention have, unexpectedly and beneficially been found to qualify as a preferred BCS (Biopharmaceutics Classification System) Class 1 substance. Additionally, they have each been found to exhibit one or more of the following unexpected and beneficial characteristics: high thermodynamic stability, chemical and physical stability in the solid state, excellent thermal properties (e.g., high melting point), and high crystallinity (as shown by data presented herein). Accordingly, the crystalline forms according to the invention may be synthesized using a crystallization process that is more efficient and results in improved particle size and morphology relative to the corresponding amorphous form of verubecestat. Employing a novel crystalline form of verubecestat according to the invention may allow the use of conventional processing methods and formulation strategies. This is significant in that crystalline API (active pharmaceutical ingredient) forms typically have a reduced physical and chemical stability risk compared to the high energy state amorphous solid dispersions. Ultimately this may allow for less protective and potentially less expensive packaging configurations. A conventional formulation also allows for the use of standard, well-known processing trains (roller compaction, blending, and compression). These standard processing trains have been optimized to provide high yield, are easily scalable, and are abundant throughout the pharmaceutical manufacturing facilities worldwide. In addition, the manufacture of non-standard formulations of verubecestat may require higher energy inputs (extrusion) or the use of solvents (e.g., spray drying). Thus, the novel crystalline forms according to the invention provide a potential for improved overall cost of goods.

Pharmaceutical Compositions

As noted above, another embodiment provides a pharmaceutical composition comprising any of the above described Crystalline Forms according to the invention. In such compositions, the Crystalline Form comprises either the sole active agent, or is optionally present in combination with one or more additional therapeutic agents. In either case, said pharmaceutical compositions can further comprise one or more pharmaceutically acceptable carriers, excepients and/or diluents. Non-limiting examples of additional therapeutic agents which may be useful in combination with a Crystalline Form according to the invention include those selected from the group consisting of: (a) drugs that may be useful for the treatment of Alzheimer's disease and/or drugs that may be useful for treating one or more symptoms of Alzheimer's disease, (b) drugs that may be useful for inhibiting the synthesis Aβ, (c) drugs that may be useful for treating neurodegenerative diseases, and (d) drugs that may be useful for the treatment of type II diabetes and/or one or more symptoms or associated pathologies thereof.

Additional non-limiting examples of therapeutic agents which may be useful in combination with a Crystalline Form according to the invention include drugs that may be useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, comprising administering to said patient at least one Crystalline Form according to the invention in an amount effective to inhibit or treat said pathology or pathologies.

Additional non-limiting examples of therapeutic agents for that may be useful in combination with a Crystalline Form according to the invention include: muscarinic antagonists (e.g., agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H-inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer).

When used in combination with additional therapeutic agents, the Crystalline Forms according to the invention and the one or more additional agents may be administered together or sequentially, as noted above. When used contemporaneously with one or more other drugs, a pharmaceutical composition in unit dosage form containing such other drugs and the Crystalline Form according to the invention is contemplated. However, the combination therapy may also include therapies in which the Crystalline Form according to the invention and one or more other drugs are administered on different overlapping schedules. It is also contemplated that when used in combination with one or more other active ingredients, the Crystalline Forms according to the invention and the other active ingredient(s)

may be used in lower doses than when each is used singly. Further, such other drugs may be administered by a route and in an amount commonly used therefor, contemporaneously or sequentially with a Crystalline Form according to the invention. When a Crystalline Form according to the invention is used contemporaneously with one or more other drugs, a pharmaceutical composition comprising such other drugs in addition to the Crystalline Form according to the invention are prepared without undue experimentation in accordance with the methods described herein and/or known in the art.

The weight ratio of a Crystalline Form according to the invention to the second active ingredient may be varied and will depend upon the effective dose of each ingredient. Generally, an effective dose of each is used. Thus, for example, when a Crystalline Form according to the invention is combined with another agent, the weight ratio of the Crystalline Form according to the invention and the second agent will generally range from about 1000:1 to about 1:1000, such as about 200:1 to about 1:200, wherein, in each case an effective dose for the intended purpose is used. Such combinations may be administered separately or concurrently, and the administration of one may be prior to, concurrent with, or subsequent to the administration of the other agent(s).

For preparing the pharmaceutical compositions described herein, pharmaceutically acceptable carriers can be solid or liquid, or in any other known dosage form such as aerosols or lotions. Non-limiting examples of solid form preparations include powders, tablets, dispersible granules, capsules, cachets and suppositories. The powders and tablets may be comprised of any of the wt % values of active ingredient described herein, and in any desired dose (e.g., doses as described herein).

The Crystalline Forms according to the invention may be presented in a dosage unit form which may be prepared by any of the methods well known in art of pharmacy. All methods include the step of bringing a Crystalline Form according to the invention into association with the carrier which constitutes accessory ingredients. In general, the pharmaceutical compositions are prepared by uniformly and intimately bringing active ingredient into association with a liquid carrier or finely divided solid carrier or both, and then, if necessary, shaping the product into the desired formulation. In the pharmaceutical composition active ingredient(s) is included in an effective amount. "Effective amount" or "therapeutically effective amount" is meant to describe an amount of Crystalline Form according to the invention effective that will elicit the biological or medical response of a tissue, system, animal or human, that is being sought by the researcher, medical doctor, veterinarian, or other clinician. It is recognized that one skilled in the art may affect the disorders by treating a patient presently afflicted with the disorders or by prophylactically treating a patient at risk for the disease or disorder with an effective amount of a Crystalline Form according to the invention. As used herein, the terms "treatment" or "treating" refer to all processes wherein there may be a slowing, interrupting, arresting, controlling, or stopping of the progression of the diseases or disorders described herein, but does not necessarily indicate a total elimination of all disorder pathologies or symptoms, as well as the prophylactic therapy of the mentioned conditions, particularly in a patient who is predisposed to such disease or disorder. In the case of Alzheimer's disease, treatments can be directed to persons who have been diagnosed with Alzheimer's disease, or those with MCI (Mild Cognitive Impairment) or Prodromal Alzheimer's disease, or as directed by the attending healthcare professional. The terms "administration of" and/or "administering a" Crystalline Form according to the invention should be understood to mean providing a Crystalline Form according to the invention, or a composition comprising a Crystalline Form according to the invention, to an individual in need thereof.

Pharmaceutical compositions intended for oral use may be prepared in accordance with methods described herein and other methods well known to art for the manufacture of pharmaceutical compositions. Such compositions may further contain active agents selected from sweetening agents, flavoring agents, coloring agents and preserving agents where pharmaceutically elegant and/or palatable preparations are desired. Tablets and capsules are contemplated. Tablets or capsules may contain active ingredient in admixture with non-toxic pharmaceutically acceptable excipients which are suitable for the manufacture of tablets. These excipients may be for example, inert diluents, such as calcium carbonate, sodium carbonate, mannitol, microcrystalline cellulose, starch, lactose (e.g., lactonse monohydrate or lactose anhydrate), calcium phosphate or sodium phosphate; granulating or disintegrating agents, for example, crospovidone, corn starch, croscarmellose sodium or alginic acid; binding agents, for example starch, hydroxypropylcellulose (HPC), silicone dioxide, gelatin or acacia, and lubricating agents, for example magnesium stearate, stearic acid or talc. Suitable solid carriers also may include magnesium carbonate, magnesium stearate, talc, sugar or lactose. Tablets, powders, cachets and capsules can be used as solid dosage forms suitable for oral administration. The tablets may be uncoated or coated by known techniques to delay disintegration and absorption in the gastrointestinal tract and thereby provide sustained action over a longer period. Compositions for oral use may also be presented as hard gelatin capsules wherein active ingredient is mixed with an inert solid diluent, for example, calcium carbonate, calcium phosphate or kaolin, or as soft gelatin capsules wherein active ingredient is mixed with water or an oil medium, for example peanut oil, liquid paraffin, or olive oil. Aqueous suspensions contain active materials in admixture with excipients suitable for the manufacture of aqueous suspensions. Dispersible powders and granules suitable for preparation of an aqueous suspension by addition of water provide active ingredient in admixture with a dispersing or wetting agent, suspending agent, and one or more preservatives.

Liquid and topical form preparations are also contemplated. Such forms include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration. Aerosol preparations suitable for inhalation are also contemplated. Such forms include solutions and solids in powder form, which may be in combination with a pharmaceutically acceptable carrier, such as an inert compressed gas, e.g. nitrogen. Solid form preparations that are intended to be converted, shortly before use, to liquid form preparations for either oral or parenteral administration are also contemplated. Such liquid forms include solutions, suspensions and emulsions. Transdermal delivery preparations are also contemplated. Transdermal compositions can take the form of creams, lotions, aerosols and/or emulsions and can be included in a transdermal patch of the matrix or reservoir type as are conventional in art for this purpose. Subcutaneous delivery forms are also contemplated. Additional examples of dosage forms, formulations, and pharmaceutically acceptable carriers and methods of manufacture for various compositions may be found in A. Gennaro (ed.), *Remington's Pharmaceutical Sciences,* 18th Edition, (1990), Mack Publishing Co., Easton, Pa.

Another embodiment provides suitable dosages and dosage forms of a Crystalline Form according to the invention and their use in the various methods described herein. Suitable doses for administering a Crystalline Form according to the invention to patients may readily be determined by those skilled in art, e.g., by an attending physician, pharmacist, or other skilled worker, and may vary according to patient health, age, weight, frequency and duration of administration, use with other active ingredients, and/or indication for which the Crystalline Form is administered. Thus, the dosage of active ingredient in the compositions of this invention may be varied, however, it is necessary that the amount of the active ingredient be such that a suitable dosage form is obtained. The doses may be administered to patients in need of such treatment in dosages that will provide optimal pharmaceutical efficacy. Doses may range from about 0.001 to 500 mg/kg (subject to tolerability limits) of body weight per day of the Crystalline Form according to the invention. In one embodiment, the dosage is from about 0.01 to about 25 mg/kg of body weight per day of a Crystalline Form according to the invention. In one embodiment, the dosage is from about 0.1 to about 1 mg/kg of body weight per day of a Crystalline Form according to the invention. In one embodiment, the dosage is from about 0.24 to about 0.8 mg/kg of body weight per day of a Crystalline Form according to the invention. In another embodiment, the quantity of active Crystalline Form in a unit dose of preparation may be varied or adjusted from about 1 mg to about 100 mg, preferably from about 1 mg to about 50 mg, more preferably from about 1 mg to about 25 mg, according to the particular application. In another embodiment, the compositions may be provided in the form of tables containing 1.0 to 1000 milligrams of the active ingredient, such as 1, 5, 10, 12, 15, 20, 25, 40, 50, 60, 75, 100, 150, 200, 250, 300, 400, 500, 600, 750, 800, 900, and 1000 milligrams of the active ingredient for the adjustment of dosage according to the degree of Aβ lowering or other biological process desired.

In one embodiment, the dose is 5 mg per dose. In such one embodiment, the Crystalline Form is Crystalline Tosylate Hydrate Form 1 and the dose is 5 mg per dose. In another such embodiment, the Crystalline Form is Crystalline Tosylate Form 2 and the dose is 5 mg per dose. In another such embodiment, the Crystalline Hemihydrate Form 1 and the dose is 5 mg per dose. In another such embodiment, the Crystalline Monohydrate Form 1 and the dose is 5 mg per dose.

In one embodiment, the dose is 10 mg per dose. In such one embodiment, the Crystalline Form is Crystalline Tosylate Hydrate Form 1 and the dose is 10 mg per dose. In another such embodiment, the Crystalline Form is Crystalline Tosylate Form 2 and the dose is 10 mg per dose. In another such embodiment, the Crystalline Hemihydrate Form 1 and the dose is 10 mg per dose. In another such embodiment, the Crystalline Monohydrate Form 1 and the dose is 10 mg per dose.

In one embodiment, the dose is 12 mg per dose. In such one embodiment, the Crystalline Form is Crystalline Tosylate Hydrate Form 1 and the dose is 12 mg per dose. In another such embodiment, the Crystalline Form is Crystalline Tosylate Form 2 and the dose is 12 mg per dose. In another such embodiment, the Crystalline Hemihydrate Form 1 and the dose is 12 mg per dose. In another such embodiment, the Crystalline Monohydrate Form 1 and the dose is 12 mg per dose.

In one embodiment, the dose is 40 mg per dose. In such one embodiment, the Crystalline Form is Crystalline Tosylate Hydrate Form 1 and the dose is 40 mg per dose. In another such embodiment, the Crystalline Form is Crystalline Tosylate Form 2 and the dose is 40 mg per dose. In another such embodiment, the Crystalline Hemihydrate Form 1 and the dose is 40 mg per dose. In another such embodiment, the Crystalline Monohydrate Form 1 and the dose is 40 mg per dose.

In one embodiment, the dose is 60 mg per dose. In such one embodiment, the Crystalline Form is Crystalline Tosylate Hydrate Form 1 and the dose is 60 mg per dose. In another such embodiment, the Crystalline Form is Crystalline Tosylate Form 2 and the dose is 60 mg per dose. In another such embodiment, the Crystalline Hemihydrate Form 1 and the dose is 60 mg per dose. In another such embodiment, the Crystalline Monohydrate Form 1 and the dose is 60 mg per dose.

In one embodiment, the dose is 100 mg per dose. In such one embodiment, the Crystalline Form is Crystalline Tosylate Hydrate Form 1 and the dose is 100 mg per dose. In another such embodiment, the Crystalline Form is Crystalline Tosylate Form 2 and the dose is 100 mg per dose. In another such embodiment, the Crystalline Hemihydrate Form 1 and the dose is 100 mg per dose. In another such embodiment, the Crystalline Monohydrate Form 1 and the dose is 100 mg per dose.

The Crystalline Form according to the invention may be formulated for administration on, e.g., a regimin of from 1 to 4 times per day, such as once or twice per day, in one embodiment once per day. In an alternative of each of the foregoing embodiments, the formulation is for once daily dosing.

In one embodiment, a dosage formulation comprises 12 mg of a Crystalline Form of Verubecestat selected from the group consisting of Crystalline Tosylate Hydrate Form 1, Crystalline Tosylate Form 2, Crystalline Hemihydrate Form 1, and Crystalline Monohydrate Form 1 of Verubecestat, further comprising lactose monohydrate, Povidone K29/32, croscarmellose sodium, and magnesium stearate.

In one embodiment, a dosage formulation comprises an intra granular layer comprising 12 mg of a Crystalline Form of Verubecestat selected from the group consisting of Crystalline Tosylate Hydrate Form 1, Crystalline Tosylate Form 2, Crystalline Hemihydrate Form 1, and Crystalline Monohydrate Form 1 of Verubecestat, further comprising lactose monohydrate, povodine, microcrystalline cellulose, and croscarmellose sodium, an extra granular layer comprising croscarmellose sodium and magnesium stearate, and optionally a film coating comprising Opadry II Blue.

In one embodiment, a dosage formulation comprises 40 mg of a Crystalline Form of Verubecestat selected from the group consisting of Crystalline Tosylate Hydrate Form 1, Crystalline Tosylate Form 2, Crystalline Hemihydrate Form 1, and Crystalline Monohydrate Form 1 of Verubecestat, further comprising lactose monohydrate, povidone, microcrystalline cellulose, croscarmellose sodium, and magnesium stearate.

In one embodiment, a dosage formulation comprises an intra granular layer comprising 40 mg of a Crystalline Form of Verubecestat selected from the group consisting of Crystalline Tosylate Hydrate Form 1, Crystalline Tosylate Form 2, Crystalline Hemihydrate Form 1, and Crystalline Monohydrate Form 1 of Verubecestat, further comprising lactose monohydrate, microcrystalline cellulose, povidone, and croscarmellose sodium, an extra granular layer comprising croscarmellose sodium and magnesium stearate, and optionally a film coating comprising Opadry II Blue.

Example 1 provides a non-limiting example of a preparation of a coated tablet comprising 12 mg Crystalline Tosylate Form 2 of Verubecestat. Example 2 provides a non-limiting example of a preparation of a coated tablet comprising 40 mg Crystalline Tosylate Form 2 of Verubecestat.

Example 1

Purified water is charged to a stainless steel container equipped with an agitator. Povidone is added into the water while being stirred to form a granulation binder solution. Lactose Monohydrate, Crystalline Tosylate Form 2, and croscarmellose sodium are charged into a blender and blended for 36 revolutions. The blended material is charged into a fluidized bed granulator. This material is fluidized and the binder solution is sprayed into the granulator to form granules. At the completion of the spraying process, the granules are dried and milled with a rotating impeller screening mill. The milled granules are charged into a diffusion-type mixer, croscarmellose sodium is added into the mixer and blended for 72 revolutions. Magnesium stearate (0.7 kg) is added into the mixer after passing through a stainless steel screen and blended for 36 revolutions. The blended material is compressed into tablet (cores) with target tablet weight of 120 mg using a rotary tablet press equipped with the product-specific tooling. The tablet cores are coated with Opadry® II film coating suspension.

Example 2

Purified water is charged to a stainless steel container equipped with an agitator. Povidone is added into the water while being stirred to form a granulation binder solution. Lactose Monohydrate, Crystalline Tosylate Form 2, and croscarmellose sodium are charged into a blender and blended for 36 revolutions. The blended material is charged into a fluidized bed granulator. This material is fluidized and the binder solution is sprayed into the granulator to form granules. At the completion of the spraying process, the granules are dried and milled with a rotating impeller screening mill. The milled granules are charged into a diffusion-type mixer, croscarmellose sodium (2.1 kg) is added into the mixer and blended for 72 revolutions. Magnesium stearate (0.7 kg) is added into the mixer after passing through a stainless steel screen and blended for 36 revolutions. The blended material is compressed into tablet (cores) with target tablet weight of 120 mg using a rotary tablet press equipped with the product-specific tooling. The tablet cores are coated with Opadry® II film coating suspension.

Methods of Use

As noted above, the scientific literature and recent clinical trials support the use of inhibitors of BACE-1 and BACE-2, including verubecestat, in a wide variety of indications, including Alzheimer's disease. In each of these embodiments, reference to administration of a Crystalline Form according to the invention, e.g., a Crystalline Form of Verubecestat selected from the group consisting of Crystalline Tosylate Hydrate Form 1, Crystalline Tosylate Form 2, Crystalline Hemihydrate Form 1, and Crystalline Monohydrate Form 1 of Verubecestat, further comprising, refers to either administration of the neat chemical or in the form of a composition as described herein.

Thus, another embodiment provides a method of inhibiting β-secretase comprising exposing a population of cells expressing β-secretase to at least one Crystalline Form according to the invention in an amount effective to inhibit β-secretase. In one such embodiment, said population of cells is in vivo. In another such embodiment, said population of cells is ex vivo. In another such embodiment, said population of cells is in vitro.

Additional embodiments in which a Crystalline Form according to the invention may be useful include: a method of inhibiting β-secretase in a patient in need thereof. A method of inhibiting the formation of Aβ from APP in a patient in need thereof. A method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one Crystalline Form according to the invention in a therapeutically effective amount to inhibit said pathology or condition in said patient.

Additional embodiments in which a Crystalline Form according to the invention may be useful include: a method of treating, preventing, and/or delaying the onset of one or more pathologies associated with Aβ and/or one or more symptoms of one or more pathologies associated with Aβ. Non-limiting examples of pathologies which may be associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, presenile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $β_2$ microglobulins and complications arising therefrom in hemodialysis patients), scrapie, bovine spongiform encephalitis, and Creutzfeld-Jakob disease, said method(s) comprising administering to said patient in need thereof at least one Crystalline Form according to the invention in an amount effective to inhibit said pathology or pathologies.

Another embodiment in which a Crystalline Form according to the invention may be useful includes a method of treating Alzheimer's disease, wherein said method comprises administering an effective amount of a Crystalline Form according to the invention, optionally in further combination with one or more additional therapeutic agents which may be effective to treat Alzheimer's disease or a disease or condition or one or more symptoms associated therewith, to a patient in need of treatment. In embodiments wherein additional therapeutic agents are administered, such agents may be administered sequentially or together, and formulated accordingly. Non-limiting examples of associated diseases or conditions, and non-limiting examples of suitable additional therapeutically active agents, are as described above.

Another embodiment in which a Crystalline Form according to the invention may be useful includes a method of treating mild cognitive impairment ("MCI"), wherein said method comprises administering an effective amount of a Crystalline Form according to the invention to a patient in need of treatment. In one such embodiment, treatment is commenced prior to the onset of symptoms.

Another embodiment in which a Crystalline Form according to the invention may be useful includes a method of preventing, or alternatively of delaying the onset, of mild cognitive impairment or, in a related embodiment, of preventing or alternatively of delaying the onset of Alzheimer's disease. In such embodiments, treatment can be initiated prior to the onset of symptoms, in some embodiments significantly before (e.g., from several months to several years before) the onset of symptoms to a patient at risk for developing MCI or Alzheimer's disease. Thus, such methods comprise administering, prior to the onset of symptoms or clinical or biological evidence of MCI or Alzheimer's disease (e.g., from several months to several years before, an effective and over a period of time and at a frequency of dose sufficient for the therapeutically effective degree of inhibition of the BACE enzyme over the period of treatment, an amount of a Crystalline Form according to the invention to a patient in need of treatment.

Another embodiment in which a Crystalline Form according to the invention may be useful includes a method of treating Down's syndrome, comprising administering an effective amount of a Crystalline Form according to the invention to a patient in need of treatment.

In another embodiment, the invention provides methods of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease. Such methods comprise administering a Crystalline Form according to the invention, or a pharmaceutically acceptable salt thereof, to a patient in need thereof in an amount effective to treat said disease or pathology.

In another embodiment, the invention provides for the use of any of the Crystalline Forms according to the invention for use as a medicament, or in medicine, or in therapy.

In another embodiment, the invention provides for use of any of the Crystalline Forms according to the invention for the manufacture of a medicament for the treatment of a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease.

We claim:

1. Crystalline Tosylate Form 2 of Verubecestat characterized by an X-ray powder diffraction pattern comprising peaks at degrees 2 theta 5.38, 8.14, 16.34, and 11.68 in a X-ray powder diffraction obtained using Cu K alpha radiation.

2. The Crystalline Tosylate Form 2 of Verubecestat according to claim 1, wherein the X-ray powder diffraction pattern further comprises diffraction peaks at degrees 2 theta 14.82, 19.48, 24.38, and 14.40.

3. The Crystalline Tosylate Form 2 of Verubecestat according to claim 2, wherein the X-ray powder diffraction pattern further comprises diffraction peaks at degrees 2 theta 23.56, 21.08, 26.98, and 30.12.

4. Crystalline Tosylate Form 2 of Verubecestat characterized by substantially the same x-ray diffraction pattern as FIG. 1.

5. Crystalline Tosylate Hydrate Form 2 of Verubecestat characterized by an X-ray powder diffraction pattern comprising peaks at degrees 2 theta 4.34, 8.78, 17.14, and 7.44 in a X-ray powder diffraction obtained using Cu K alpha radiation.

6. The Crystalline Tosylate Hydrate Form 2 of Verubecestat according to claim 5, wherein the X-ray powder diffraction pattern further comprises diffraction peaks at degrees 2 theta 11.32, 19.32, 18.38, and 10.76.

7. The Crystalline Tosylate Hydrate Form 2 of Verubecestat according to claim 6, wherein the X-ray powder diffraction pattern further comprises diffraction peaks at degrees 2 theta 17.72, 14.00, 15.08, and 13.26.

8. Crystalline Tosylate Hydrate Form 2 of Verubecestat characterized by substantially the same x-ray diffraction pattern as FIG. 4.

9. Crystalline Hemihydrate Form 2 of Verubecestat characterized by an X-ray powder diffraction pattern comprising peaks at degrees 2 theta 25.88, 20.58, 12.82, and 9.56 in a X-ray powder diffraction obtained using Cu K alpha radiation.

10. The Crystalline Hemihydrate Form 2 of Verubecestat according to claim 9, wherein the X-ray powder diffraction pattern further comprises diffraction peaks at degrees 2 theta 24.18, 18.12, 13.48, and 21.78.

11. The Crystalline Hemihydrate Form 2 of Verubecestat according to claim 10, wherein the X-ray powder diffraction pattern further comprises diffraction peaks at degrees 2 theta 15.04, 22.08, 28.68, and 19.18.

12. Crystalline Hemihydrate Form 2 of Verubecestat characterized by substantially the same x-ray diffraction pattern as FIG. 7.

13. Crystalline Monohydrate Form 2 of Verubecestat characterized by an X-ray powder diffraction pattern comprising peaks at degrees 2 theta 8.66, 9.15, 11.38, and 12.29 in a X-ray powder diffraction obtained using Cu K alpha radiation.

14. The Crystalline Monohydrate Form 2 of Verubecestat according to claim 13, wherein the X-ray powder diffraction pattern further comprises diffraction peaks at degrees 2 theta 13.72, 14.75, 18.83, and 19.72.

15. The Crystalline Monohydrate Form 2 of Verubecestat according to claim 14, wherein the X-ray powder diffraction pattern further comprises diffraction peaks at degrees 2 theta 20.35, 20.96, 22.77, and 24.66.

16. Crystalline Monohydrate Form 2 of Verubecestat characterized by substantially the same x-ray diffraction pattern as FIG. 10.

17. A pharmaceutical composition comprising the Crystalline Form of Verubecestat according to claim 1 and a pharmaceutically acceptable carrier.

18. A method of treating an Aβ pathology or one or more symptoms thereof, wherein said Aβ pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease, said method comprising administering the Crystalline Form of Verubecestat according to claim 1 to a person in need thereof in an amount effective to treat said disease or pathology.

19. The method of claim 18, wherein disease or pathology is Alzheimer's disease.

\* \* \* \* \*